United States Patent
Sato et al.

(10) Patent No.: US 7,601,801 B2
(45) Date of Patent: Oct. 13, 2009

(54) HLA-A24 BINDING CANCER ANTIGEN PEPTIDE DERIVED FROM LIVIN

(75) Inventors: Noriyuki Sato, Sapporo (JP); Toshihiko Torigoe, Sapporo (JP); Hiroyuki Hariu, Sapporo (JP); Yoshihiko Hirohashi, Wakayama-ken (JP)

(73) Assignee: Dainippon Sumitomo Pharma Co., Ltd., Osaka-Fu (JP)

( * ) Notice: Subject to any disclaimer, the term of this patent is extended or adjusted under 35 U.S.C. 154(b) by 186 days.

(21) Appl. No.: 10/563,916

(22) PCT Filed: Jul. 7, 2004

(86) PCT No.: PCT/JP2004/010008

§ 371 (c)(1),
(2), (4) Date: Jan. 10, 2006

(87) PCT Pub. No.: WO2005/005631

PCT Pub. Date: Jan. 20, 2005

(65) Prior Publication Data

US 2007/0036812 A1 Feb. 15, 2007

(30) Foreign Application Priority Data

Jul. 11, 2003 (JP) .............................. 2003-273236

(51) Int. Cl.
C07K 16/00 (2006.01)
A61K 38/00 (2006.01)

(52) U.S. Cl. ....................... 530/328; 530/327

(58) Field of Classification Search ....................... None
See application file for complete search history.

(56) References Cited

U.S. PATENT DOCUMENTS

| 2003/0087319 A1 | 5/2003 | Gomes et al. | |
| 2003/0157522 A1 | 8/2003 | Boudreault et al. | |
| 2007/0036811 A1* | 2/2007 | Straten et al. | 424/185.1 |

FOREIGN PATENT DOCUMENTS

| JP | 2002-284797 A | 10/2002 | |
| JP | 2002-316998 A | 10/2002 | |
| WO | WO 00/77201 A1 | 12/2000 | |
| WO | WO 03/040172 A2 | 5/2003 | |
| WO | WO 2004/089980 | * | 10/2004 |

OTHER PUBLICATIONS

Schmollinger et al PNAS vol. 100 p. 3398 (2003).*
Essell (J. NIH Res. 1995 7:46).*
Spitler (Cancer Biotherapy, 1995, 10:1-3).*
Boon (Adv. Can. Res. 1992 58:177-210).*
Lee et al, J. Immunology vol. 163 p. 6296 (1999).*
Balch et al., Arch. Surg. vol. 125, pp. 200-205, (1990).
Anichini et al., Immunology Today, vol. 8, No. 12, pp. 385-389, (1987).
Muul et al., The Journal of Immunology, vol. 138, No. 3, pp. 989-995, (1987).
Ioth et al., Int. J. Cancer, vol. 52, pp. 52-59 (1992).
Rosenberg et al., Journal of the National Cancer Institute, vol. 86, No. 15, pp. 1159-1166 (1994).
Van Der Bruggen et a., Science, vol. 254, pp. 1643-1647, (1991).
Boon et al., Immunology Today, vol. 18, No. 6, pp. 267,268, (1997).
Boon et al., J. Exp. Med. vol. 183, pp. 725-729 (1996).
Robbins et al., Curr. Opin. Immunol., vol. 8 pp. 628-636 (1996).
Vucic et al., Curr. Biol., vol. 10., No. 21, pp. 1359-1366 (2000).
NCBI database Accession NO AAG33622, pp. 9.
Rammensee et al., Immunogenetics, vol. 41, pp. 178-228 (1995).
Kondo et al., J. Immunology, vol. 155, pp. 4307-4312 (1995).
Kubo et al., J. Immunol. vol. 152, pp. 3913-3924, (1994).
Kast et al., J. Immunol. vol. 152, pp. 3904-3912, (1994).
Schmollinger JC. et al., Natl. Acad. Sci. USA., Mar. 18, 2003, vol. 100, No. 6, pp. 3398 to 3403.
Kasof GM. et al., J. Biol. Chem. (2001), vol. 276, No. 5, pp. 3238 to 3246.

* cited by examiner

*Primary Examiner*—Sheela J Huff
(74) *Attorney, Agent, or Firm*—Birch, Stewart, Kolasch & Birch, LLP

(57) ABSTRACT

The present invention provides a partial peptide consisting of 8-11 contiguous amino acids in the amino acid sequence of livin set forth in SEQ ID NO: 1, which binds to HLA-A24 antigen and is recognized by cytotoxic T cells (CTLs), a polynucleotide encoding the peptide, and cancer vaccine comprising the peptide or the polynucleotide.

5 Claims, 2 Drawing Sheets

HLA-A24 BINDING CANCER ANTIGEN PEPTIDE DERIVED FROM LIVIN

TECHNICAL FIELD

The present invention relates to HLA-A24 binding cancer antigen peptides.

BACKGROUND ART

It is known that the immune system, particularly T cells, plays an important role in the elimination of cancer (tumor) by a living body. Indeed, infiltration of lymphocytes exhibiting cytotoxic actions on cancer cells in human cancer foci has been observed (*Arch. Surg.*, 126: p 200, 1990), and cytotoxic T lymphocytes (CTLs) recognizing autologous tumor cells have been isolated from melanomas without great difficulties (e.g., *Immunol. Today,* 8: p 385, 1987; *J. Immunol.,* 138: p 989, 1987; and *Int. J. Cancer,* 52: p 52, 1992). In addition, the results of clinical treatment of melanomas by transfer of the CTLs also suggested the importance of T cells in cancer elimination (*J. Natl. Cancer. Inst.,* 86: p 1159, 1994).

Although the target molecules of CTLs attacking autologous tumor cells had long been unclear, such molecules have become clearer gradually as the advance in immunology and molecular biology in recent years. Specifically, it has been revealed that CTLs recognize a complex between a peptide, called cancer antigen peptide, and a major histocompatibility complex class I antigen (MHC class I antigen, also referred to as HLA antigen) through the T cell receptors (TCRs), and thereby attacking autologous tumor cells.

Cancer antigen peptides are generated by intracellular proteasomal degradation of cancer-specific antigen proteins after synthesis in cells. The cancer antigen peptides thus generated bind to MHC class I antigens (HLA antigens) in endoplasmic reticulum to form complexes, and the complexes are transported to the cell surface to be presented as an antigen. Antigen-specific CTLs recognize the complex presented as an antigen, and exhibits anti-cancer effects through the cytotoxic action or production of lymphokines. As a consequence of elucidation of a series of the actions, it has become possible to treat cancer by using cancer antigen protein or a cancer antigen peptide as a so-called cancer vaccine to enhance cancer-specific CTLs in the body of a cancer patient.

As a cancer antigen protein, T. Boon et al. identified a protein named MAGE from human melanoma cells for the first time in 1991 (*Science,* 254: p 1643, 1991). Subsequently, several additional cancer antigen proteins have been identified mainly from melanoma cells. Examples of melanoma antigens that have been identified are melanosomal proteins such as a melanocytic tissue-specific protein, gp100, MART-1 and tyrosinase, MEGE-related proteins that are expressed not only on melanomas but also on various cancer cells and normal testicular cells; β-catenin having a cancer-specific amino acid mutation; and CDK4. Cancer antigen proteins other than those from melanomas have also been identified including products of oncogenes such as HER2/neu and p 53 (variant); cancer markers such as CEA and PSA; and viral proteins such as HPV and EBV. Detailed descriptions of these substances can be found in published reviews (e.g. *Immunol. Today,* 18: p 267, 1997; *J. Exp. Med.,* 183: p725, 1996; and *Curr. Opin. Immunol.,* 8: p 628, 1996).

Livin has been identified as a molecule belonging to an inhibitor of apoptosis protein (IAP) family (*J. Biol. Chem.* 276: p 3238, 2001). Livin consists of 280 amino acids and has a singe unique repeated sequence of about 70 amino acids called a baculoviral IAP repeat (BIR). ML-IAP (melanoma inhibitor of apoptosis protein) which is a molecule identified as an IAP highly expressed by melanomas around the same time has the same amino acid sequence as livin (*Curr. Biol.* 10: p 1359, 2000).

It was reported that T cells isolated from metastatic focus of melanoma of an HLA-A*0201-positive patient recognized ML-IAP-derived peptides and exerted cytotoxic activity, and hence livin was presumed to be a target of cytotoxic T cells (CTLs) as a cancer antigen protein (*Proc. Natl. Acad. Sci. USA,* 100: p 3398, 2003). However, it has not been elucidated whether or not livin contains a peptide portion(s) capable of binding to HLA-A24 antigen among a number of HLA antigens.

DISCLOSURE OF THE INVENTION

The purpose of the present invention is to provide HLA-A24 binding cancer antigen peptides derived from livin and use of the peptide as cancer vaccine, and the like.

The present inventors have conducted intensive study on livin-derived antigen peptides possibly usable as cancer vaccine in cancer immunotherapy. In consequence, the present inventors have for the first time found that livin contains a cancer antigen peptide portion(s) which binds to HLA-A24 antigen among a number of HLA antigen subclasses and is recognized by CTLs. This finding led to the development of novel cancer vaccine therapy whereby livin-specific CTLs can be induced in HLA-A24-positive cancer patients.

Specifically, the present inventors have found that the cancer antigen peptide identified by SEQ ID NO: 8 exhibits particularly higher HLA-A24-antigen-binding activity and better CTL-inducing activity compared to a positive control, and is suited for clinical use.

The present inventor has been established on the basis of these findings.

Thus, the present invention encompasses the followings.

(1) A peptide consisting of 8-11 contiguous amino acids in the amino acid sequence of livin set forth in SEQ ID NO: 1, which binds to HLA-A24 antigen and is recognized by CTLs.

(2) The peptide of (1) above, which comprises an amino acid sequence set forth in any one of SEQ ID NOS: 2-59.

(3) The peptide of (2) above, which consists of an amino acid sequence set forth in any one of SEQ ID NOS: 2-59.

(4) The peptide of (2) above, which comprises an amino acid sequence set forth in any one of SEQ ID NOS: 6-9.

(5) The peptide of (4) above, which consists of an amino acid sequence set forth in any one of SEQ ID NOS: 6-9.

(6) The peptide of (4) above, which comprises the amino acid sequence set forth in SEQ ID NO: 8.

(7) The peptide of (6) above, which consists of the amino acid sequence set forth in SEQ ID NO: 8.

(8) A peptide of 9-11 amino acids which comprises an amino acid sequence wherein the amino acid residue at position 2 and/or C-terminus of an amino acid sequence set forth in any one of SEQ ID NOS: 2-59 is substituted by another amino acid residue, and which binds to an HLA-A24 antigen and is recognized by CTLs.

(9) The peptide of (8) above, which consists of an amino acid sequence wherein the amino acid residue at position 2 and/or C-terminus of an amino acid sequence set forth in any one of SEQ ID NOS: 2-59 is substituted by another amino acid residue.

(10) The peptide of (8) above, which comprises an amino acid sequence wherein the amino acid residue at position 2 and/or C-terminus of an amino acid sequence set forth in any one of SEQ ID NOS: 2-59 is substituted by an amino acid residue selected from the following amino acids:

tyrosine, phenylalanine, methionine and tryptophan for the position 2; and phenylalanine, leucine, isoleucine, tryptophan and methionine for the C-terminus.

(11) The peptide of (10) above, which consists of an amino acid sequence wherein the amino acid residue at position 2 and/or C-terminus of an amino acid sequence set forth in any one of SEQ ID NOS: 2-59 is substituted by an amino acid residue selected from the following amino acids:
tyrosine, phenylalanine, methionine and tryptophan for the position 2; and phenylalanine, leucine, isoleucine, tryptophan and methionine for the C-terminus.

(12) The peptide of (10) above, which comprises an amino acid sequence wherein the amino acid residue at position 2 and/or C-terminus of an amino acid sequence set forth in any one of SEQ ID NOS: 6-9 is substituted by an amino acid residue selected from the following amino acids:
tyrosine, phenylalanine, methionine and tryptophan for the position 2; and phenylalanine, leucine, isoleucine, tryptophan and methionine for the C-terminus.

(13) The peptide of (12) above, which consists of an amino acid sequence wherein the amino acid residue at position 2 and/or C-terminus of an amino acid sequence set forth in any one of SEQ ID NOS: 6-9 is substituted by an amino acid residue selected from the following amino acids:
tyrosine, phenylalanine, methionine and tryptophan for the position 2; and phenylalanine, leucine, isoleucine, tryptophan and methionine for the C-terminus.

(14) The peptide of (12) above, which comprises an amino acid sequence wherein the amino acid residue at position 2 and/or C-terminus of the amino acid sequence set forth in SEQ ID NO: 8 is substituted by an amino acid residue selected from the following amino acids:
tyrosine, phenylalanine, methionine and tryptophan for the position 2; and phenylalanine, leucine, isoleucine, tryptophan and methionine for the C-terminus,
as identified in SEQ ID NO: 63, with the proviso that the amino acid sequence of SEQ ID NO: 8 is excluded.

(15) The peptide of (14) above, which consists of an amino acid sequence wherein the amino acid residue at position 2 and/or C-terminus of the amino acid sequence set forth in SEQ ID NO: 8 is substituted by an amino acid residue selected from the following amino acids:
tyrosine, phenylalanine, methionine and tryptophan for the position 2; and phenylalanine, leucine, isoleucine, tryptophan and methionine for the C-terminus, as identified in SEQ ID NO: 63, with the proviso that the amino acid sequence of SEQ ID NO: 8 is excluded.

(16) An epitope peptide comprising a peptide of any one of (1) to (15) above.

(17) A peptide dimer in which peptide monomers described in any one of (1) to (16) above and containing a cysteine residue(s) are bound through a disulfide bond.

(18) The peptide dimer of (17) above, in which peptide monomers comprising an amino acid sequence set forth in any one of SEQ ID NOS: 7-9 are bound through a disulfide bond.

(19) The peptide dimer of (18) above, in which peptide monomers comprising the amino acid sequence set forth in SEQ ID NO: 8 are bound through a disulfide bond.

(20) A polynucleotide encoding a peptide described in any one of (1) to (16) above.

(21) An expression vector containing the polynucleotide described in (20) above.

(22) A cell containing the expression vector described in (21) above.

(23) A process for producing a peptide described in any one of (1) to (19) above, which comprises culturing the cell described in (22) above under the condition where the peptide can be expressed.

(24) An antibody which specifically binds to a peptide described in any one of (1) to (19) above.

(25) An antigen-presenting cell which presents a complex between a peptide described in any one of (1) to (19) above and HLA-A24 antigen.

(26) The antigen-presenting cell of (25) above, which presents a complex of a peptide comprising an amino acid sequence set forth in any one of SEQ ID NOS: 6-9 and HLA-A24 antigen.

(27) The antigen-presenting cell of (26) above, which presents a complex of a peptide comprising the amino acid sequence set forth in SEQ ID NO: 8 and HLA-A24 antigen.

(28) A CTL which recognizes a complex between a peptide described in any one of (1) to (19) above and HLA-A24 antigen.

(29) The CTL of (28) above, which recognizes a complex between a peptide comprising an amino acid sequence set forth in any one of SEQ ID NOS: 6-9 and HLA-A24 antigen.

(30) The CTL of (29) above, which recognizes a complex between a peptide comprising the amino acid sequence set forth in SEQ ID NO: 8 and HLA-A24 antigen.

(31) A pharmaceutical composition which comprises a peptide described in any one of (1) to (19) above, an expression vector described in (21) above, a cell described in (22) above, an antigen-presenting cell described in any one of (25) to (27) above, or a CTL described in any one of (28) to (30) above, together with a pharmaceutically acceptable carrier.

(32) The pharmaceutical composition of (31) above, which is used as a CTL inducer.

(33) The pharmaceutical composition of (31) above, which is used as cancer vaccine.

(34) A diagnosing agent for cancer which comprises an antibody described in (24) above.

(35) An HLA monomer, dimer, tetramer or pentamer comprising a peptide described in any one of (1) to (19) above together with HLA-A24 antigen.

(36) The HLA monomer, dimer, tetramer or pentamer of (35) above, which comprises a peptide comprising an amino acid sequence set forth in any one of SEQ ID NOS: 6-9 together with HLA-A24 antigen.

(37) The HLA monomer, dimer, tetramer or pentamer of (36) above, which comprises a peptide comprising the amino acid sequence set forth in SEQ ID NO: 8 together with HLA-A24 antigen.

(38) A reagent for the detection of CTLs specific for an HLA-A24-binding cancer antigen peptide derived from livin, which reagent comprises an HLA monomer, dimer, tetramer or pentamer described in any one of (35) to (37) above as an ingredient.

(39) The reagent of (38) above, which is used in the assessment of effects of cancer vaccine.

BEST MODE FOR CARRYING OUT THE INVENTION

Figure 1:
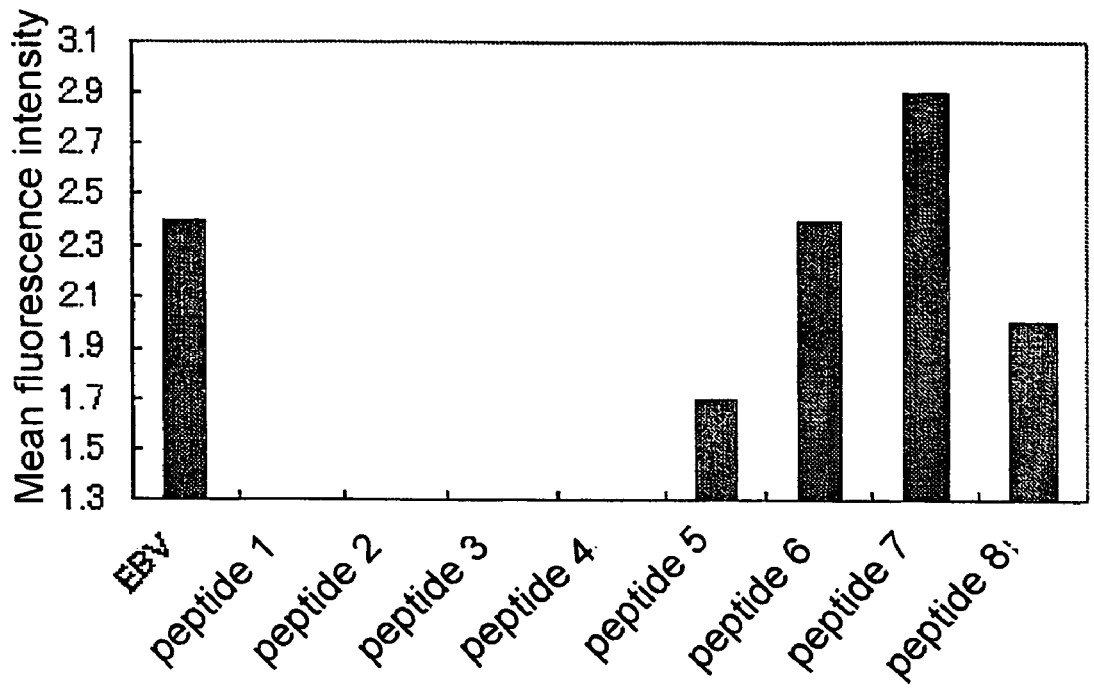
FIG. 1 is a graph showing the binding affinity to HLA-A*2402 of eight peptides derived from livin and EBV, a peptide derived from EV virus, as a positive control. In the figure, the vertical axis shows mean values of fluorescence intensity (binding affinity) (Example 1).

The present invention provides a peptide consisting of 8-11 contiguous amino acids in the amino acid sequence of livin set forth in SEQ ID NO: 1, which binds to HLA-A24 antigen and is recognized by CTLs.

The peptide of the present invention comprises a part of the amino acid sequence set forth in SEQ ID NO: 1, as mentioned above; however, N-terminal and/or C-terminal amino acid residue may be modified. Further, when a peptide contains a cysteine residue, it may be in the form of dimer wherein monomers bind through a disulfide bond.

The amino acid sequence of human livin set forth in SEQ ID NO: 1 is a known sequence described in *J. Biol. Chem.* 276: 3238, 2001 and NCBI database Accession No. AAG33622.

The peptide of the present invention is a peptide which consists of 8-11 contiguous amino acids in the amino acid sequence of human livin set forth in SEQ ID NO: 1. The definition of "8-11 amino acids" is based on the facts that peptides having an activity of binding to HLA-A24 antigen generally consist of 8 to 11 amino acids (*Immunogenetics*, 41: 178-228, 1995, *J. Immunol.*, 155: 4307-4312, 1995, *J. Immunol.*, 152: 3913-3924, 1994, *J. Immunol.*, 152: 3904-3912, 1994). Preferred peptides are those consisting of 9-11 contiguous amino acids, and more preferably, 9-10 contiguous amino acids in the amino acid sequence of human livin set forth in SEQ ID NO: 1.

The peptide of the present invention can be identified by synthesizing a partial peptide (candidate peptide) consisting of 8-11 contiguous amino acids in the amino acid sequence set forth in SEQ ID NO: 1, and assaying whether or not the peptide is capable of binding to HLA-A24 antigen and being recognized by CTLs.

The synthesis of a peptide can be conducted according to processes generally used in the field of peptide chemistry. Such a method can be found in literatures including *Peptide Synthesis*, Interscience, New York, 1966; *The Proteins*, Vol. 2, Academic Press Inc., New York, 1976; *Peptide Synthesis*, Maruzen, Inc., 1975; *Peptide-Gosei no Kiso to Jikken*, Maruzen, Inc., 1985; and *Iyakuhim no Kaihatsu* (Zoku), Vol. 14, Peptide Synthesis, Hirokawa-syoten, 1991.

As used hereinbefore, the phrase "binds to HLA-A24 antigen and is recognized by CTLs" means that a peptide has an activity as a cancer antigen peptide, which has the same meaning as "binds to HLA-A24 antigen and induces CTLs (having a CTL-inducing activity)", or "binds to HLA-A24 antigen and activates CTLs (having a CTL-activating activity)". Accordingly, the phrase "binds to HLA-A24 antigen and is recognized by CTLs" may be expressed as "having an activity as a cancer antigen peptide" or "having a CTL-inducing activity".

It can be examined by a method described in, for example, *J. Immunol.*, 169, 1611, 2002 whether "a candidate peptide binds to HLA-A24 antigen and is recognized by CTLs".

Specifically, peripheral blood mononuclear cells (PBMCs) are first isolated from a human subject positive for HLA-A24 antigen and cultured. After cultivation, nonadherent cells are recovered and cultured. From the culture, T cell population (CD8-positive T cells) including CTLs is separated using anti-CD8 antibody immobilized on magnetic beads or the like. Separately, for the preparation of antigen-presenting cells, adherent cells are cultured, and after addition (pulse) of a candidate peptide, the cells are further cultured.

The peptide-pulsed antigen-presenting cells and T cell population including CTLs are mix-cultured. After amplifying peptide-specific CTLs by repeated stimulation with peptide-pulsed antigen-presenting cells, the cytotoxic activity of said CTLs is measured by, for example, $^{51}$Cr release assay (*Int. J. Cancer*, 58: p 317, 1994) or the like. Examples of target cell usable in the assay include $^{51}$Cr-labeled cells which are positive for livin and positive for HLA-A24. Specific examples include $^{51}$Cr-labeled cells which are obtained by introducing a gene encoding HLA-A*2402 (*Cancer Res.*, 55: 4248-4252 (1995), Genbank Accession No. M64740), a subclass of HLA-A24, into a cell line derived from melanoma or lung cancer which is positive for livin and negative for HLA-A24.

When target cells are injured by CTLs in the above assay, the candidate peptide is evaluated to have the activity, "binds to HLA-A24 antigen and is recognized by CTLs", of the present invention.

In addition, whether or not the candidate peptide has the activity of the present invention, "binds to HLA-A24 antigen and is recognized by CTLs", can be confirmed by using an HLA-A24 model mouse described in WO02/47474 and *Int. J. Cancer*, 100, 565-570, 2002.

It has been known that there are many subtypes of HLA molecule and that the amino acid sequence of antigen peptides capable of binding thereto obeys a certain rule (binding motif). Regarding the binding motif for HLA-A24, it is known that, in a 8- to 11-amino-acid peptides, the amino acid at position 2 is tyrosine (Tyr), phenylalanine (Phe), methionine (Met) or tryptophan (Trp), and the amino acid at the C-terminus is phenylalanine (Phe), leucine (Leu), isoleucine (Ile), tryptophan (Trp) or methionine (Met) (*Immunogenetics*, 41: p 178-228, 1995, *J. Immunol.*, 155: p 4307-4312, 1995, *J. Immunol.*, 152: p 3913-3924, 1994, *J. Immunol.*, 152: p 3904-3912, 1994). In addition, amino acid residues analogous to the above-mentioned amino acid residues involved in those motifs are also available.

Recently, it has become possible to search for peptide sequences that are expected to be able to bind to HLA antigen using BIMAS software of NIH through the internet (http://bimas.dcrt.nih.gov/molbio/hlabind/).

The present invention is based on the finding that livin (SEQ ID NO: 1) contains antigen peptide portions which bind to HLA-A24 antigen and are recognized by CTLs, for the first time. Examples of putative HLA-A24-binding amino acid sequences of 9 or 10 amino acids identified by screening the amino acid sequence of livin with the aforementioned BIMAS software include the partial amino acid sequences of livin set forth in SEQ ID NOS: 2-59.

Thus, as a specific embodiment of the peptide of the present invention, the present invention provides a peptide comprising an amino acid sequence set forth in any one of SEQ ID NOS: 2-59, which binds to HLA-A24 antigen and is recognized by CTLs.

There are no limitations regarding the length of such a peptide on the condition that said peptide is a partial peptide of livin, comprises an amino acid sequence set forth in any one of SEQ ID NOS: 2-59, and has an activity of binding to HLA-A24 antigen and being recognized by CTLs. However, since a peptide having a binding activity to HLA-A24 antigen is known to generally consist of 8 to 11 amino acids (*Immunogenetics*, 41: p 178-228, 1995, *J. Immunol.*, 155: p 4307-4312, 1995, *J. Immunol.*, 152: p 3913-3924, 1994, *J. Immunol.*, 152: p 3904-3912, 1994), the peptides of the present invention as defined by the afore-mentioned sequence identifier numbers preferably consist of 9-11, more preferably, 9-10 amino acids.

As a more preferred embodiment of the peptides of the present invention, the present invention provides a peptide consisting of 9-11, preferably 9-10 amino acids, which comprises an amino acid sequence set forth in any one of SEQ ID NOS: 2-59, and which binds to HLA-A24 antigen and is recognized by CTLs.

As a still more preferred embodiment, the present invention provides a peptide consisting of an amino acid sequence set forth in any one of SEQ ID NOS: 2-59, which binds to HLA-A24 antigen and is recognized by CTLs.

Among the peptides of the present invention defined by the aforementioned sequence identifier numbers, those each comprising the amino acid sequence set forth in SEQ ID NOS: 6-9 are preferred, and those comprising the amino acid sequence set forth in SEQ ID NO: 8 are particularly preferred. The cancer antigen peptide set forth in SEQ ID NO: 8 has been found by the present inventors as a peptide exhibiting particularly higher HLA-A24 antigen-binding activity and better CTL-inducing activity compared to a positive control.

The length of a peptide is preferably 9-11, and more preferably, 9-10 amino acids. Peptides consisting of an amino acid sequence set forth in SEQ ID NOS: 6-9 are preferred and those consisting of the amino acid sequence of SEQ ID NO: 8 are especially preferred.

The peptides of the present invention may be altered as appropriate within a range that the activity is maintained. As used herein the "alteration" of amino acid residue means substitution, deletion and/or addition of amino acid residue(s) (the addition is inclusive of addition of amino acid(s) at the N- and/or C-terminus of a peptide). The substitution of amino acid residue(s) is preferred. When the alteration involves substitution of an amino acid residue(s), any number of amino acid residues at any position can be replaced on the condition that the activity as cancer antigen peptide is retained. However, since a peptide which binds to HLA-A24 antigen is generally about 8-11 amino acid in length, the alteration is preferably involves one to several amino acids.

When altering amino acid residue by substitution, it is preferred that the amino acid residue at position 2 and/or C-terminus is substituted in a peptide having the structure for the binding motif of HLA-A24 antigen.

Specific examples of substitution-related peptides of the present invention include peptides of 9-11 amino acids (preferably, 9-10 amino acids), which comprise an amino acid sequence wherein the amino acid residue at position 2 and/or C-terminus of an amino acid sequence set forth in any one of SEQ ID NOS: 2-59 is substituted by another amino acid residue, and which bind to an HLA-A24 antigen and are recognized by CTLs.

Above all, peptides which consist of an amino acid sequence wherein the amino acid residue at position 2 and/or C-terminus of an amino acid sequence set forth in any one of SEQ ID NOS: 2-59 is substituted by another amino acid residue and which bind to an HLA-A24 antigen and are recognized by CTLs are preferred.

In the substitution above, it is preferred to use as a substitute(s). an amino acid residue(s) that retains the structure for the binding motif of HLA-A24 antigen. Thus, preferred examples of substitution-related peptides of the present invention include peptides of 9-11 amino acids (preferably, 9-10 amino acids), which comprise an amino acid sequence wherein the amino acid residue at position 2 and/or C-terminus of an amino acid sequence set forth in any one of SEQ ID NOS: 2-59 is substituted by an amino acid residue selected from the following amino acids:

tyrosine, phenylalanine, methionine and tryptophan for the position 2; and phenylalanine, leucine, isoleucine, tryptophan and methionine for the C-terminus, and which bind to HLA-A24 antigen and are recognized by CTLs.

More preferred examples of substitution-related peptides include peptides which consist of an amino acid sequence wherein the amino acid residue at position 2 and/or C-terminus of an amino acid sequence set forth in any one of SEQ ID NOS: 2-59 is substituted by an amino acid residue selected from the following amino acids:

tyrosine, phenylalanine, methionine and tryptophan for the position 2; and phenylalanine, leucine, isoleucine, tryptophan and methionine for the C-terminus, and which bind to HLA-A24 antigen and are recognized by CTLs.

Further preferred examples of substitution-related peptides include peptides of 9-11 amino acids (preferably, 9-10 amino acids), which comprise an amino acid sequence wherein the amino acid residue at position 2 and/or C-terminus of an amino acid sequence set forth in any one of SEQ ID NOS: 6-9 is substituted by an amino acid residue selected from the following amino acids:

tyrosine, phenylalanine, methionine and tryptophan for the position 2; and phenylalanine, leucine, isoleucine, tryptophan and methionine for the C-terminus, and which bind to HLA-A24 antigen and are recognized by CTLs.

Still more preferred examples of substitution-related peptides include peptides which consist of an amino acid sequence wherein the amino acid residue at position 2 and/or C-terminus of an amino acid sequence set forth in any one of SEQ ID NOS: 6-9 is substituted by an amino acid residue selected from the following amino acids:

tyrosine, phenylalanine, methionine and tryptophan for the position 2; and phenylalanine, leucine, isoleucine, tryptophan and methionine for the C-terminus, and which bind to HLA-A24 antigen and are recognized by CTLs.

Particularly preferred examples of substitution-related peptides include peptides of 9-11 amino acids (preferably, 9-10 amino acids), which comprise an amino acid sequence wherein the amino acid residue at position 2 and/or C-terminus of the amino acid sequence set forth in SEQ ID NO: 8 is substituted by an amino acid residue selected from the following amino acids:

tyrosine, phenylalanine, methionine and tryptophan for the position 2; and phenylalanine, leucine, isoleucine, tryptophan and methionine for the C-terminus, as identified in SEQ ID NO: 63, with the proviso that the amino acid sequence of SEQ ID NO: 8 is excluded, and which bind to HLA-A24 antigen and are recognized by CTLs.

More particularly preferred examples of substitution-related peptides include peptides which consist of an amino acid sequence wherein the amino acid residue at position 2 and/or C-terminus of the amino acid sequence set forth in SEQ ID NO: 8 is substituted by an amino acid residue selected from the following amino acids:

tyrosine, phenylalanine, methionine and tryptophan for the position 2; and phenylalanine, leucine, isoleucine, tryptophan and methionine for the C-terminus, as identified in SEQ ID NO: 63, with the proviso that the amino acid sequence of SEQ ID NO: 8 is excluded, and which bind to HLA-A24 antigen and are recognized by CTLs.

The alteration (preferably, substitution) of amino acid residue at position 2 and/or the C-terminus can be conducted for the purpose of improving the binding activity to HLA-A24 antigen or enhancing the activity of the above-mentioned natural-type tumor antigen peptides of the present invention which consist of partial sequences of livin. The parts other than the substituted amino acid at position 2 and/or the C-terminus of a peptide may remain to have the natural-type sequence (i.e., being kept to have the same sequence as livin), or may be further altered as far as the activity is retained. Specifically, such alteration may involve the replacement of cysteine residue by another amino acid residue (e.g., serine, alanine, α-aminobutyric acid). More specifically, examples include peptides obtained by replacing cysteine at position 6 of a peptide by another amino acid (e.g., serine, alanine or α-aminobutyric acid), which peptide is a peptide having the amino acid sequence set forth in SEQ ID NO: 7 or a substitute-type peptide derived therefrom by substitution at position 2 and/or the C-terminus in the amino acid sequence of SEQ ID NO: 7. Another examples of such peptides include those obtained by replacing cysteine at position 6 of a peptide by another amino acid (e.g., serine, alanine or α-aminobutyric acid), which peptide is a peptide having the amino acid sequence set forth in SEQ ID NO: 8 or is a substitute-type peptide derived therefrom by substitution at position 2 and/or the C-terminus in the amino acid sequence of SEQ ID NO: 8 (e.g., peptide identified by SEQ ID NO: 63). Still another examples of such peptides include those obtained by replacing cysteine at position 7 of a peptide by another amino acid (e.g., serine, alanine or α-aminobutyric acid), which peptide is a peptide having the amino acid sequence set forth in SEQ ID NO: 9 or is a substitute-type peptide derived therefrom by substitution at position 2 and/or the C-terminus in the amino acid sequence of SEQ ID NO: 9.

The peptide of the present invention also provides a peptide (so-called an epitope peptide) comprising a peptide (natural- or altered-peptide) of the present invention together with a helper peptide or another cancer antigen peptide.

Recently, a peptide ("epitope peptide") composed of multiple (plural) CTL epitopes (antigen peptides) linked together has been shown to have an activity of inducing CTLs efficiently. For example, it has been reported that a peptide (about 30-mer) wherein CTL epitopes each restricted to HLA-A2-, -A3, -A11 or B53 originated from tumor antigen protein PSA are ligated together induced in vivo CTLs specific for respective CTL epitopes (*Journal of Immunology* 1998, 161: 3186-3194).

In addition, a peptide (epitope peptide) wherein a CTL epitope(s) and a helper epitope(s) are ligated has been shown to induce CTLs efficiently. In this context, "helper epitope" means a peptide capable of activating a CD4-positive T cells (*Immunity.*, 1:751, 1994), and examples thereof include HBVc128-140 of hepatitis B virus origin, TT947-967 of tetanus toxin origin, etc. CD4+ T cells activated by said helper epitope exert various activities including induction and maintenance of CTLs, differentiation, and activation of effectors such as macrophages, etc, and hence are considered to be important in the immunological anti-tumor response. As a concrete example of a peptide wherein a helper epitope(s) and CTL epitope(s) are linked together, it is reported that a DNA (minigene) encoding a peptide composed of HBV-originated HLA-A2-restricted antigen peptides (6 peptides), HLA-A11-restricted antigen peptides (3 peptides) and a helper epitope induced in vivo CTLs directed to the respective epitopes efficiently (*Journal of Immunology* 1999, 162: 3915-3925). Practically, a peptide wherein a CTL epitope (tumor antigen peptide corresponding to position 280-288 of melanoma antigen gp 100) and a helper epitope (tetanus toxin-originated T helper epitope) are ligated has been subjected to clinical test (*Clinical Cancer Res.*, 2001, 7:3012-3024).

Accordingly, as a specific embodiment, the peptides of the present invention also include epitope peptides in which multiple epitopes including the aforementioned peptides of the present invention (natural- or altered-peptides) are ligated and which have a CTL-inducing activity.

When the epitope to be ligated to the cancer antigen peptide of the present invention is a CTL epitope (cancer antigen peptide), examples of CTL epitopes usable include livin-derived CTL epitopes restricted to HLA-A0201, -A0204, -A0205, -A0206, or -A0207. Plural numbers of these CTL epitopes can be linked together, and the length of one CTL epitope may be about 8-14 amino acids on the basis of the analysis of antigen peptides bound to various HLA molecules (*Immunogenetics*, 41: 178, 1995).

When the epitope to be ligated to the cancer antigen peptide of the present invention is a helper epitope, examples of helper epitopes usable include the aforementioned HBVc128-140 of hepatitis B virus origin, TT947-967 of tetanus toxin origin, etc. The helper epitope may be about 13-30 amino acids, preferably, about 13-17 amino acids in length.

Specifically, examples of an epitope peptide of the present invention include epitope peptides wherein one or more peptides consisting of an amino acid sequence set forth in any one of SEQ ID NOS: 2-59, which bind to HLA-A24 antigen and are recognized by CTLs are ligated to a helper epitope.

More specifically, examples include an epitope peptide wherein a peptide consisting of the amino acid sequence set forth in SEQ ID NO: 8 is ligated to either a tetanus toxin-originated helper peptide (e.g., Phe Asn Asn Phe Thr Val Ser Phe Trp Leu Arg Val Pro Lys Val Ser Ala Ser His Leu Glu; SEQ ID NO: 61) or a peptide (Ala Gln Tyr Ile Lys Ala Asn Ser Lys Phe Ile Gly Ile Thr Glu Leu; SEQ ID NO: 62. Clinical Cancer Res., 2001, 7: 3012-3024), and the like.

The peptide (epitope peptide) wherein multiple epitopes are ligated can be prepared by aforementioned usual method for peptide synthesis. It can also be prepared by a usual method for DNA synthesis and genetic engineering on the basis of sequence information of a polynucleotide encoding an epitope peptide wherein multiple epitopes are ligated. Specifically, an epitope peptide wherein a multiple epitopes are ligated can be prepared by inserting a polynucleotide encoding the peptide into a known expression vector, transforming a host cell with the resultant recombinant expression vector, culturing the transformants, and recovering the objective peptide from the culture. These processes can be conducted according to, for example, a method described in a literature (*Molecular Cloning*, T. Maniatis et al., CSH Laboratory (1983), *DNA Cloning*, D M. Glover, IRL PRESS (1985)), or that described hereinafter.

The so produced epitope peptide wherein multiple epitopes are ligated can be examined for the CTL-inducing activity by the above-mentioned $^{51}$Cr release assay or by subjecting to model animals for human described in WO02/47474 or *Int J. Cancer.* 100, 565-570, 2002.

Also, the amino group of the N-terminal amino acid or the carboxyl group of the C-terminal amino acid of the above-identified peptide of the present invention (natural-, altered- or epitope-peptide) can be modified. The peptides wherein the N-terminal and/or C-terminal amino acid residue is modified fall within the scope of the peptide of the present invention.

Examples of a group for the modification of amino group of the N-terminal amino acid include 1 to 3 groups selected from $C_{1-6}$ alkyl group, phenyl group, cycloalkyl group and acyl group. Acyl groups include $C_{1-6}$ alkanoyl group, $C_{1-6}$ alkanoyl group substituted by phenyl group, carbonyl group substituted by $C_{5-7}$ cycloalkyl group, $C_{1-6}$ alkylsulfonyl group, phenylsulfonyl group, $C_{2-6}$ alkoxycarbonyl group, alkoxycarbonyl group substituted by phenyl group, carbonyl group substituted by $C_{5-7}$ cycloalkoxy group, phenoxycarbonyl group, and the like.

Examples of peptides modified at the carboxyl group of C-terminal amino acid include esters and amides. Esters include $C_{1-6}$ alkyl esters, $C_{0-6}$ alkyl esters substituted by phenyl group, $C_{5-7}$ cycloalkyl esters, and the like. Amides specifically include amides, amides substituted by one or two $C_{1-6}$ alkyl groups, amides substituted by one or two $C_{0-6}$ alkyl groups that are substituted by phenyl group, amides forming 5- to 7-membered azacycloalkane inclusive of nitrogen atom of amide group, and the like.

Further, when the above-mentioned peptide of the present invention (natural-, altered- or epitope-peptide) contains a cysteine residue, the peptide monomer may form a dimer through the disulfide bond. Said dimer can be obtained by synthesizing a peptide monomer and placing the resulting peptide monomer under oxidation conditions.

Specific examples include dimers of a peptide consisting of the amino acid sequence set forth in SEQ ID NO: 7 or a substitute-type peptide derived therefrom by substitution of the amino acid at position 2 and/or the C-terminus. Another example includes dimers of a peptide consisting of the amino acid set forth in SEQ ID NO: 8 or a substitute-type peptide derived therefrom by substitution of the amino acid at position 2 and/or the C-terminus (e.g., peptide identified by SEQ ID NO: 63). Still another example includes dimers of a peptide consisting of the amino acid set forth in SEQ ID NO: 9 or a substitute-type peptide derived therefrom by substitution of the amino acid at position 2 and/or the C-terminus.

The present invention also provides a polynucleotide encoding the above-mentioned peptide (natural-, altered- or epitope-peptide) of the present invention. The polynucleotide encoding a peptide of the present invention may be in the form of DNA or RNA. The polynucleotides of the present invention can be easily prepared on the basis of information about amino acid sequence of the present peptide or polynucleotide sequence of DNA encoding the same. Specifically, synthesis can be carried out using usual method of DNA synthesis or amplification by PCR.

In particular, examples include a polynucleotide encoding an epitope peptide wherein one or more peptides consisting of an amino acid sequence set forth in any one of SEQ ID NOS: 2-59 which bind to HLA-A24 antigen and are recognized by CTLs are ligated to a helper epitope.

Preferred examples include a polynucleotide encoding an epitope peptide wherein a peptide consisting of the amino acid sequence set forth in SEQ ID NO: 8 is ligated to a tetanus toxin-originated helper peptide (e.g., Phe Asn Asn Phe Thr Val Ser Phe Trp Leu Arg Val Pro Lys Val Ser Ala Ser His Leu Glu; SEQ ID NO: 61). Also included is a polynucleotide encoding an epitope peptide wherein a peptide consisting of the amino acid sequence set forth in SEQ ID NO: 8 is ligated to a peptide: Ala Gln Tyr Ile Lys Ala Asn Ser Lys Phe Ile Gly Ile Thr Glu Leu (SEQ ID NO: 62, *Clinical Cancer Res.*, 2001, 7: 3012-3024).

A recombinant expression vector for expressing the peptide of the present invention can be constructed by incorporating a polynucleotide prepared in the above into an expression vector.

An adequate expression vector can be selected depending on the host to be used, purposes, and the like, and include plasmids, phage vectors, virus vectors, and the like.

When the host is *Escherichia coli*, examples of vector include plasmid vectors such as pUC118, pUC119, pBR322, pCR3, and the like; and phage vectors such as λZAPII, λgt11, and the like. When the host is yeast, examples of vector include pYES2, pYEUra3, and the like. When the host is insect cells, examples of vector include pAcSGHisNT-A, etc. When the host is animal cells, examples of vector include plasmid vectors such as pKCR, pCDM8, pGL2, pcDNA3.1, pRc/RSV, pRc/CMV, and the like; and virus vectors such as retrovirus vector, adenovirus vector, adeno-associated virus vector, and the like.

The expression vector may optionally contain a factor(s) such as promoter capable of inducing expression, a gene encoding a signal sequence, a marker gene for selection, terminator, and the like.

Furthermore, the expression vector may contain an additional sequence for expressing the peptide as a fusion protein with thioredoxin, His tag, GST (glutathione S-transferase), or the like, so as to facilitate the isolation and purification. Vectors usable in such a case include GST fusion protein vectors containing an appropriate promoter (lac, tac, trc, trp, CMV, SV40 early promoter, etc) that functions in host cells, such as pGEX4T; vectors containing Tag sequence (Myc, His, etc) such as pcDNA3.1/Myc-His; and vectors capable of expressing a fusion protein between thioredoxin and His tag such as pET32a.

Transformed cells containing the vector of the present invention can be prepared by transforming host cells with an expression vector obtained in the above.

Host cells usable herein include *Escherichia coli*, yeast, insect cells and animal cells. Examples of *Escherichia coli* include strains of *E. coli* K-12 such as HB101, C600, JM109, DH5α and AD494 (DE3). Examples of yeast include *Saccharomyces cerevisiae*. Examples of animal cells include L929, BALB/c3T3, C127, CHO, COS, Vero and Hela cells. Examples of insect cells include sf9.

Introduction of an expression vector into host cells can be done using a conventional method suited for the respective host cells above. Specifically, introduction can be done using calcium phosphate method, DEAE-dextran method, electroporation method, and a method using lipid for gene transfer (Lipofectamine Lipofectin; Gibco-BRL). Following the introduction, the cells are cultured in a conventional medium containing a selection marker, whereby transformants containing the expression vector can be selected.

The peptide of the present invention can be produced by culturing the transformed cells under appropriate conditions (conditions under which peptides can be expressed). The resultant peptide may be further isolated and purified according to standard biochemical purification procedures. The purification procedures include salting out, ion exchange chromatography, absorption chromatography, affinity chromatography, gel filtration chromatography, etc. When the polypeptide of the present invention has been expressed as a fusion peptide with thioredoxin, His tag, GST, or the like, as mentioned above, the peptide can be isolated and purified by appropriate purification procedures making use of the characteristics of the fusion protein or tags.

The present invention provides an antibody which specifically binds to a peptide of the present invention. The antibody of the present invention is not restricted to any form and may be polyclonal or monoclonal antibody raised against a peptide of the present invention as an antigen.

As mentioned above, there is no limitation regarding the antibody of the present invention on the condition that it specifically binds to a peptide of present invention. Examples of antibody include those specifically bind to a peptide consisting of an amino acid sequence set forth in any one of SEQ ID NOS: 2-59 which binds to HLA-A24 antigen and is recognized by CTLs. Antibodies specifically bind to a peptide consisting of an amino acid sequence set forth in any one of SEQ ID NOS: 6-9 are preferred, and those specifically bind to a peptide consisting of the amino acid sequence set forth in SEQ ID NO: 8 are especially preferred.

Methods of preparation of antibodies are well known in the art and the antibodies of the present invention can be prepared according to any one of conventional methods (*Current protocols in Molecular Biology* edit. Ausubel et al. (1987) Publish. John Wiley and Sons. Section 11.12-11.13, Antibodies; *A Laboratory Manual*, Lane, H, D. et al., ed., Cold Spring Harbor Laboratory Press, New York 1989).

Specifically, the antibodies of the present invention can be obtained by immunizing non-human animal such as rabbit using a peptide of the present invention as an antigen, and recovering the antibodies from serum of the immunized animal in a conventional manner. In the case of monoclonal antibodies, they can be obtained by immunizing non-human animal such as mouse with a peptide of the present invention, subjecting the resultant splenocytes to cell fusion with myeloma cells, and recovering antibodies from the resultant hybridoma cells (*Current protocols in Molecular Biology* edit. Ausubel et al. (1987) Publish. John Wiley and Sons. Section 11.4-11.11).

The antibodies against the peptide of the present invention can also be produced while enhancing the immunological response using different adjuvants depending on the host. Examples of adjuvants include Freund adjuvants; mineral gels such as aluminium hydroxide; surfactants such as lysolecithin, Pluronic® polyol, polyanion, peptide, oil emulsion, keyhole limpet hemocyanin and dinitorophenol; human adjuvants such as BCG (Bacille de Calmette-Guerin) or Corynebacterium, etc.

As mentioned above, antibodies that recognize a peptide of the present invention and antibodies that neutralize the activity thereof can easily be prepared by immunizing an animal in a conventional manner. The antibodies may be used in affinity chromatography, immunological diagnostic method, and the like. Immunological diagnostic method may be selected as appropriate from immunoblotting, radioimmunoassay (RIA), enzyme-linked immunosorbent assay (ELISA), a fluorescent or luminescent assay, and the like. The immunological diagnostic method is effective in the diagnosis of cancer expressing livin gene such as lung cancer, colon cancer, prostate cancer, renal cancer, gastric cancer, melanoma (especially, malignant melanoma), clear cell sarcoma, and the like.

The present invention provides an antigen-presenting cell A which presents a complex between a peptide of the present invention and HLA-A24 antigen.

As shown in the Examples below, it was observed that stimulation with a peptide of the present invention led to exertion of CTL-inducing activity, which indicates that there existed antigen-presenting cells presenting a complex between a peptide of the present invention and HLA-A24 antigen and that CTLs specifically recognizing said antigen-presenting cells were induced. Such antigen-presenting cells presenting a complex between HLA-A24 antigen and a peptide of the present invention are used effectively in the cell therapy (DC therapy) as hereinafter described.

The antigen-presenting cells of the present invention include any cells presenting a complex of HLA-A24 antigen and a peptide of the present invention, and specifically those wherein a complex between HLA-A24 antigen and a peptide consisting of an amino acid sequence set forth in any one of SEQ ID NOS: 2-59 which binds to HLA-A24 antigen and is recognized by CTLs is presented on the cell surface of dendritic cells. Antigen presenting cells wherein a complex between HLA-A24 antigen and a peptide consisting of an amino acid sequence set forth in any one of SEQ ID NOS: 6-9 is presented on the cell surface of dendritic cells are preferred and those wherein a complex between a peptide consisting of the amino acid sequence set forth in SEQ ID NO: 8 and HLA-A24 antigen is presented on the cell surface of dendritic cells are more preferred.

The antigen-presenting cells used in the cell therapy (DC therapy) can be prepared by isolating cells having antigen-presenting ability from a cancer patient, pulsing the cells in vitro with a peptide of the present invention, or introducing into the cells a polynucleotide or an expression vector containing the same of the present invention, and allowing the cells to present a complex between HLA-A24 antigen and a cancer antigen peptide derived from the peptide of the present invention. The "cells having antigen-presenting ability" are not limited to particular cells and may be any cells expressing HLA-A24 antigen capable of presenting a peptide of the present invention on the cell surface; however, dendritic cells known to have especially high antigen-presenting ability are preferred.

Further, the substances with which antigen-presenting cells are pulsed may be a peptide of the present invention, or a polynucleotide encoding the peptide of the present invention or an expression vector containing the same.

The antigen-presenting cells of the present invention can be prepared by, for example, isolating cells having antigen-presenting ability from a cancer patient, pulsing the cells in vitro with a peptide of the present invention (e.g., a tumor antigen peptide consisting of the amino acid sequence set forth in SEQ ID NO: 8), thereby producing a complex between HLA-A24 antigen and the peptide of the present invention (*Cancer Immunol. Immunother.*, 46:82, 1998, *J. Immunol.*, 158: p 1796, 1997, *Cancer Res.*, 59: p 1184, 1999). When dendritic cells are used, antigen-presenting cells of the present invention can be prepared by, for example, isolating lymphocytes from peripheral blood of a cancer patient by Ficoll method, removing non-adherent cells, incubating the adherent cells in the presence of GM-CSF and IL-4 to induce dendritic cells, and pulsing the dendritic cells by incubating with a peptide of the present invention.

In the case where antigen-presenting cells of the present invention are prepared by introducing a polynucleotide encoding a peptide of the present invention (e.g., a polynucleotide encoding an epitope peptide having the amino acid sequence set forth in SEQ ID NO: 8) or an expression vector containing the same into the aforementioned cells having an antigen-presenting ability, the preparation can be carried out, when the polynucleotide is DNA, according to a method described in *Cancer Res.*, 56: p 5672, 1996 or *J. Immunol.*, 161:p 5607, 1998, or the like. The preparation of antigen-presenting cells can be effected using RNA as well as DNA in a similar manner according to the method described in *J. Exp. Med.*, 184: p 465, 1996, or the like.

The present invention also provides CTLs which recognize a complex between a peptide of the present invention and HLA-A24 antigen.

As shown in the Examples below, it was observed that stimulation with a peptide of the present invention led to exertion of CTL-inducing activity. This indicates that there existed antigen-presenting cells presenting a complex between a peptide of the present invention and HLA-A24 antigen and that CTLs specifically recognize said antigen-presenting cells were induced. CTLs which specifically recognize a complex between HLA-A24 antigen and a peptide of the present invention can be used effectively in the adoptive immunotherapy as hereinafter described.

The CTLs of the present invention include any CTLs which specifically recognize a complex of HLA-A24 antigen and a peptide of the present invention. In particular, examples include CTLs which specifically recognize a complex between HLA-A24 antigen and a peptide consisting of an amino acid sequence set forth in any one of SEQ ID NOS: 2-59 which binds to HLA-A24 antigen and is recognized by CTLs. The CTLs which specifically recognize a complex between HLA-A24 antigen and a peptide consisting of an amino acid sequence set forth in any one of SEQ ID NOS: 6-9 are preferred, and those which specifically recognize a complex between HLA-A24 antigen and a peptide consisting of the amino acid sequence set forth in SEQ ID NO: 8 are more preferred.

The CTLs used in the adoptive immunotherapy can be prepared by isolating peripheral blood lymphocytes from a patient, stimulating the cells in vitro with a peptide of the present invention (e.g., a cancer antigen peptide consisting of the amino acid sequence set forth in SEQ ID NO: 8), or a polynucleotide encoding a peptide of the present invention (e.g., a polynucleotide encoding an epitope peptide having the amino acid sequence set forth in SEQ ID NO: 8) or an expression vector containing the same (*Journal of Experimental Medicine* 1999, 190: 1669).

The above-described peptides, expression vectors, cells, antigen-presenting cells and CTLs of the present invention can be used as an active ingredient of a CTL-inducer, i.e., cancer vaccine, by formulating into an appropriate form depending on the respective substances, as hereinafter described in more detail.

(1) Cancer Vaccine Comprising as an Active Ingredient a Peptide of the Present Invention The peptide of the present invention has a CTL-inducing ability and the so induced CTLs can exert the anti-cancer activity through cytotoxic action or production of lymphokines. The peptide of the present invention therefore can be used as an active ingredient of cancer vaccine for treating or preventing cancer. Thus, the present invention provides cancer vaccine (pharmaceutical composition as cancer vaccine) comprising as an active ingredient a peptide of the present invention. When cancer vaccine of the present invention is administered to an HLA-A24-positive and livin-positive patient, the peptide (e.g., cancer antigen peptide consisting of the amino acid sequence set forth in SEQ ID NO: 8) is presented to HLA-A24 antigen. Then, CTLs specifically recognizing the presented HLA-A24 antigen complex can proliferate and destroy the cancer cells, whereby the treatment or prevention of cancer becomes possible. The cancer vaccine of the present invention can be used in the prevention or treatment of cancer accompanied by elevated expression level of livin gene, for example, lung cancer, colon cancer, prostate cancer, renal cancer, gastric cancer, melanoma (especially, malignant melanoma), clear cell sarcoma, and the like.

In another embodiment, the present invention provides a method of treating or preventing cancer, which comprises administering an effective amount of cancer vaccine of the present invention to an HLA-A24-positive and livin-positive patient.

The cancer vaccine comprising as an active ingredient a peptide of the present invention may contain a single CTL epitope (e.g., a tumor antigen peptide consisting of the amino acid sequence set forth in SEQ ID NO: 8) or an epitope peptide wherein a peptide is ligated with other peptide(s) (CTL epitope, helper epitope, etc.) as an active ingredient. Recently, it has been shown that an epitope peptide wherein multiple CTL epitopes (antigen peptides) are linked can induce CTLs efficiently. For example, it was reported that about 30-mer epitope peptide wherein CTL epitopes restricted to HLA-A2-, -A3, -A11 or B53 originated from tumor antigen protein PSA are ligated induced CTLs specific for respective CTL epitopes (*Journal of Immunology* 1998, 161: 3186-3194). It has also been reported that an epitope peptide wherein a CTL epitope(s) and a helper epitope(s) are ligated can induce CTLs efficiently. When an epitope peptide in these forms is administered, said peptide is incorporated into antigen-presenting cells; the respective antigen peptides generated by intracellular degradation bind to HLA antigen to form complexes; the complexes are presented on the surface of antigen-presenting cells in high density; and CTLs specific for the complexes efficiently proliferate in the body and destroy cancer cells. In this way, the treatment or prevention of cancer is achieved.

The cancer vaccine comprising as an active ingredient a peptide of the present invention may be administered together with a pharmaceutically acceptable carrier, for example, an appropriate adjuvant, or in the form of particles so that the cellular immunity can be established effectively. As an adjuvant, those described in a literature (*Clin. Microbiol. Rev.*, 7:277-289, 1994), and the like are applicable. Concrete examples include microorganism-derived components, cytokines, plant-derived components, marine organism-derived components, mineral gels such as aluminium hydroxide, surfactants such as lysolecithin and Pluronic® polyols, polyanions, peptides, oil emulsion (emulsion preparations) and the like. Liposomal preparations, particulate preparations in which the ingredient is bound to beads having a diameter of several μm, preparations in which the ingredient is attached to lipids, and the like, are also contemplated.

Administration may be achieved, for example, intradermally, subcutaneously, intramuscularly, or intravenously. Although the dosage of the peptide of the present invention in the formulation may be adjusted as appropriate depending on, for example, the disease to be treated, the age and the body weight of a patient, it is usually within the range of 0.0001 mg-1000 mg, preferably 0.001 mg-1000 mg, more preferably 0.1 mg-10 mg, which can be preferably administered once in every several days to every several months.

(2) Cancer Vaccine Comprising as an Active Ingredient an Expression Vector Containing a Polynucleotide Encoding a Peptide of the Present Invention Not only the above-mentioned peptide of the present invention but also an expression vector containing a polynucleotide encoding a peptide of the present invention can be an active ingredient of DNA vaccine for treating or preventing cancer. Thus, the present invention provides cancer vaccine (pharmaceutical composition as cancer vaccine) comprising as an active ingredient an expression vector containing a polynucleotide encoding a peptide of the present invention. In another embodiment, the present invention provides a method of treating or preventing cancer, which comprises administering an effective amount of DNA vaccine of the present invention to an HLA-A24-positive and livin-positive patient.

Recently, a polynucleotide encoding an epitope peptide wherein multiple (plural) CTL epitopes (antigen peptides) are ligated or wherein a CTL epitope(s) and a helper epitope(s) are ligated has been shown to induce CTLs in vivo efficiently. For example, it is reported that a DNA (minigene) encoding an epitope peptide wherein HBV-originated HLA-A2-restricted antigen peptides (6 peptides), HLA-A11-restricted antigen peptides (3 peptides) and a helper epitope are ligated induced in vivo CTLs directed to the respective epitopes efficiently (*Journal of Immunology* 1999, 162: 3915-3925).

Accordingly, an active ingredient of cancer vaccine can be obtained by incorporating a polynucleotide encoding an epitope peptide of the present invention into an appropriate expression vector.

When administering an expression vector containing a polynucleotide of the present invention as an active ingredient of cancer vaccine (DNA vaccine), the following methods can be used.

As a method for introducing a polynucleotide of the present invention into cells, any means including those utilizing viral vectors or other methods are applicable (*Nikkei-Science*, April, 1994, 20-45; *Gekkan-Yakuji*, 36(1), 23-48 (1994); *Jikken-Igaku-Zokan*, 12(15), 1994, and references cited therein).

Examples of means utilizing a viral vector include those wherein a DNA of the present invention is incorporated into DNA or RNA virus such as retrovirus, adenovirus, adeno-associated virus, herpes virus, vaccinia virus, poxvirus, poliovirus, or Sindbis virus, and then introduced into cells. Above all, a method utilizing retrovirus, adenovirus, adeno-associated virus, or vaccinia virus, or the like, is particularly preferred.

Examples of other methods include those wherein an expression plasmid is directly injected intramuscularly (DNA vaccination), liposome method, Lipofectin method, microinjection, calcium phosphate method and electroporation. DNA vaccination and liposome method are particularly preferred.

Regarding a method to make the polynucleotide of the present invention act as a medicament in practice, there are an in vivo method wherein the polynucleotide is directly introduced into the body and an ex vivo method wherein the DNA is introduced extracorporeally into a certain cells removed from human, and the cells are reintroduced into the body (*Nikkei-Science*, April, 1994, 20-45; *Gekkan-Yakuji*, 36(1), 23-48 (1994); *Jikkenn-Igaku-Zokan*, 12(15), 1994; and references cited therein). The in vivo method is more preferred.

In the case of in vivo method, the administration can be effected through any appropriate routes depending on the disease and symptoms to be treated. For example, it may be administered via intravenous, intraarterial, subcutaneous, intracutaneous, intramuscular route, or the like. When the administration is carried out by in vivo method, the compositions may be administered in various forms such as solution, and are typically formulated, for example, in the form of injection containing, as an active ingredient, an expression vector containing a polynucleotide of the present invention to which conventional carriers may also be added, if necessary. As for the liposomes or membrane-fused liposomes (such as Sendai virus (HVJ)-liposomes) containing an expression vector containing a polynucleotide of the present invention, they may be in the form of liposomal formulation such as suspension, frozen drug, centrifugally-concentrated frozen drug, or the like.

Although the content of an expression vector containing a polynucleotide in a formulation may be adjusted as appropriate depending on, for example, the disease to be treated, age and body weight of a patient, usually, 0.0001 mg-100 mg, preferably 0.001 mg-10 mg of an expression vector containing a polynucleotide of the present invention can be administered once in every several days to every several months.

When the above-mentioned expression vector containing a polynucleotide of the present invention is administered to a cancer patient, a polypeptide corresponding to the said polynucleotide is highly expressed in antigen-presenting cells. Thereafter, cancer antigen peptides generated by intracellular degradation form complexes with HLA antigen; the complexes are then presented on the surface of antigen-presenting cells in high density; and CTLs specifically recognize said complex are efficiently proliferate in the body, and destroy cancer cells. In this way, treatment or prevention of cancer is achieved. The cancer vaccine comprising as an active ingredient an expression vector containing a polynucleotide of the present invention can be used in the prevention or treatment of cancer accompanied by elevated expression level of livin gene, for example, lung cancer, colon cancer, prostate cancer, renal cancer, gastric cancer, melanoma (especially, malignant melanoma), clear cell sarcoma, and the like.

(3) Cancer Vaccine Comprising as an Active Ingredient Antigen-presenting Cells of the Present Invention The present invention provides cancer vaccine comprising as an active ingredient antigen-presenting cells of the present invention.

Recently, a cell therapy (DC therapy) which comprises isolating lymphocytes from peripheral blood of a cancer patient, inducing dendritic cells from the lymphocytes, pulsing the dendritic cells with a peptide or the like in vitro, and reintroducing the resultant antigen-presenting cells into the patient by subcutaneous injection or the like has been reported (*Cancer Immunol. Immunother.*, 46:82, 1998, *J. Immunol.*, 158: p 1796, 1997 *Cancer Res.*, 59: p 1184, 1999, *Cancer Res.*, 56: p 5672, 1996, *J. Immunol.*, 161: p 5607, 1998, *J. Exp. Med.*, 184: p 465, 1996). The above-described antigen-presenting cells of the present invention therefore can be used as an active ingredient of cancer vaccine to be used in the cell therapy.

The cancer vaccine comprising as an active ingredient antigen-presenting cells of the present invention preferably contains physiological saline, phosphate buffered saline (PBS), medium, or the like, to stably maintain the antigen-presenting cells. It may be administered, for example, intravenously, subcutaneously, or intradermally. The dose is similar to that described in the references cited above.

When the cancer vaccine above is reintroduced into a patient's body, specific CTLs are efficiently induced in the body of a patient positive for HLA-A24 and positive for livin, whereby treatment or prevention of cancer can be effected. The cancer vaccine comprising as an active ingredient antigen-presenting cells of the present invention can be used in the prevention or treatment of cancer accompanied by elevated expression level of livin gene, for example, lung cancer, colon cancer, prostate cancer, renal cancer, gastric cancer, melanoma (especially, malignant melanoma), clear cell sarcoma, and the like.

(4) Cancer Vaccine Comprising as an Active Ingredient CTLs of the Present Invention The present invention provides cancer vaccine (pharmaceutical composition as cancer vaccine) comprising as an active ingredient CTLs of the present invention. CTLs of the present invention can be used effectively in the adoptive immunotherapy as hereinafter described.

For melanomas, therapeutic effect has been observed in adoptive immunotherapy wherein tumor-infiltrating T cells are removed from a patient and cultured ex vivo in large quantities, and returned into the same patient (*J. Natl. Cancer. Inst.*, 86: 1159, 1994). Further, in mouse melanoma, suppression of metastasis has been observed when splenocytes were stimulated with cancer antigen peptide TRP-2 in vitro to amplify CTLs specific for the cancer antigen peptide, and the CTLs are administered to a melanoma-grafted mouse (*J. Exp. Med.*, 185:453, 1997). This resulted from in vitro proliferation of CTLs that specifically recognize a complex between an HLA antigen of antigen-presenting cells and a cancer antigen peptide. Accordingly, a therapeutic method comprising stimulating in vitro peripheral blood lymphocytes from a patient with a peptide, or a polynucleotide or an expression vector of the present invention to proliferate cancer-specific CTLs, and returning the CTLs into the patient is believed to be effective. Thus, the CTLs of the present invention can be used as an active ingredient of cancer vaccine in the adoptive immunotherapy.

The cancer vaccine comprising as an active ingredient CTLs of the present invention preferably contains physiological saline, phosphate buffered saline (PBS), medium, or the like to stably maintain CTLs. It may be administered, for example, intravenously, subcutaneously or intradermally. The dose is similar to that described in the references cited above.

By returning the cancer vaccine into a patient positive for HLA-A24 and positive for livin, the cytotoxic action of CTLs on cancer cells is enhanced in the body of a patient, and the cancer cells are killed. In this way, cancer can be treated. The cancer vaccine comprising as an active ingredient CTLs of the present invention can be used in the prevention or treatment of cancer accompanied by elevated expression level of livin gene, for example, lung cancer, colon cancer, prostate cancer, renal cancer, gastric cancer, melanoma (especially, malignant melanoma), clear cell sarcoma, and the like.

The present invention provides diagnostic agent comprising an antibody of the present invention.

It is possible to conduct immunodiagnosis of cancer by means of diagnostic agent comprising an antibody of the present invention. To carry out immunodiagnosis, an antibody of the present invention is labeled as appropriate. The presence or absence of cancer can be examined by detecting antigen (livin) or antigen peptide (livin-derived antigen peptide) in a sample (e.g., blood, cancer tissue) obtained from a subject suspected to have cancer using the labeled antibody. Specifically, immunodiagnosis can be effected by immunoblotting, radioimmunoassay (RIA), enzyme-linked immunosorbent assay (ELISA), a fluorescent or luminescent assay, and the like.

The present invention also provides an HLA monomer, an HLA dimer, an HLA tetramer or an HLA pentamer comprising a peptide of the present invention and HLA-A24 antigen.

In the cancer immunotherapy, significant indicators for selecting a patient highly responsive to the cancer antigen (cancer antigen peptide), monitoring the therapeutic effects, or evaluating the suitability of treatment can be obtained through the examination of the frequency or amount of CTL precursor cells directed to a cancer antigen (cancer antigen peptide) in a patient before initiation of treatment, or the examination of the frequency or amount of CTLs in a patient undergoing treatment with the cancer antigen (cancer antigen peptide). An HLA monomer, an HLA dimer, an HLA tetramer and an HLA pentamer each comprising a tumor antigen peptide and HLA antigen are useful as a reagent in the detection of CTLs specific for antigen (antigen peptide), specifically, in the measurement of frequency or amount of CTLs.

As used herein, the HLA tetramer refers to a tetramer prepared by biotinylating a complex (HLA monomer) obtained by association of an HLA antigen α-chain and a β2-microglobulin with a peptide (antigen peptide), and allowing to bind to avidin for tetramerization (*Science* 279: 2103-2106 (1998); and *Science* 274: 94-96 (1996)).

The HLA monomer is a monomer that is used in the preparation of the above-mentioned HLA tetramer and is formed by biotinylating an association of HLA antigen α-chain, β2-microglobulin and antigen peptide.

The HLA dimer is a dimer prepared by fusing HLA antigen α-chain and Ig (immunoglobulin, for example, IgG1), and binding the resultant fusion to β2-microglobulin and antigen peptide (*Proc. Natl. Acad. Sci.* USA 90: 6671-6675 (1993)). The antigen peptide-specific CTLs bound to HLA dimer can be detected by, for example, allowing labeled anti-IgG1 antibody to bind to IgG1.

The HLA pentamer is a recently developed technique and refers to a pentamer wherein five molecules of a complex comprising HLA antigen and antigen peptide are polymerized through Coiled-Coil domain. Since the HLA antigen-antigen peptide complex can be labeled with fluorescence or the like, the analysis can be carried out by flow cytometry or the like similarly to HLA tetramer (see, http://www.proimmune.co.uk/).

The aforementioned HLA-monomer, dimer, tetramer and pentamer are all available by custom production from a manufacture such as ProImmune or BD Biosciences. At present, HLA tetramers and the like which comprise different antigen peptides are commercially available (Medical & Biological Laboratories Co., Ltd., etc.)

Examples of the HLA monomer, dimer, tetramer and pentamer of the present invention, specifically, include HLA monomers, dimers, tetramers and pentamers each comprising a peptide consisting of an amino acid sequence set forth in any one of SEQ ID NOS: 2-59 which binds to HLA-A24 antigen and is recognized by CTLs, together with HLA-A24 antigen. Above all, an HLA tetramer or an HLA pentamer is preferred, and an HLA tetramer is more preferred. In particular, an HLA tetramer and an HLA pentamer comprising a peptide consisting of an amino acid sequence set forth in any one of SEQ ID NOS: 6-9 together with HLA-A24 antigen are preferred, and an HLA tetramer and an HLA pentamer comprising a peptide consisting of the amino acid sequence set forth in SEQ ID NO: 8 together with HLA-A24 antigen are more preferred. Above all, an HLA tetramer is most preferred.

The HLA monomer, HLA tetramer and HLA pentamer are preferably labeled with fluorescence so that the bound CTLs can be easily sorted out or detected by a known detection measure such as flow cytometry, fluorescent microscopy, and the like. Examples include HLA monomers, tetramers and dimers labeled with phycoerythrin(PE), fluorescein isothiocyanate (FITC), peridinyl chlorophyll protein (PerCP), allophycocyanin (APC), or the like.

The HLA-A24 antigen (HLA-A24 antigen α-chain) which is a component of the HLA monomer, dimer, tetramer and pentamer of the present invention can be cloned easily by a conventional method such as PCR on the basis of information about known base sequence of HLA-A2402 disclosed in *Cancer Res.*, 55: 4248-4252 (1995) and Genbank Accession No. M64740.

The β2-microglobulin which is a component of the HLA monomer, dimer, tetramer and pentamer of the present invention is preferably originated from human. The human β2-microglobulin can be cloned easily by a conventional method such as PCR on the basis of information about known base sequence of human β2-microglobulin disclosed in Genbank Accession No. AB021288.

The process for the preparation of HLA monomer, dimer, tetramer and pentamer is well known from the respective literatures mentioned above; however, the preparation will be hereinafter described briefly regarding HLA tetramer.

First, an appropriate host cells such as *E. coli* or mammalian cells capable of expressing a protein is transformed with an HLA-A24 α-chain expression vector and a β2-microglobulin expression vector, and allowed to express. *E. coli* (e.g., BL21) is preferably used here. The resultant monomer HLA-A24 complex and a peptide of the present invention are then mixed to form a soluble HLA-peptide complex. The C-terminal sequence of HLA-A24 α-chain of the resultant HLA-peptide complex is biotinylated with BirA enzyme. When a biotinylated HLA-peptide complex and a fluorescently labeled avidin are mixed at the molar ratio of 4:1, an HLA tetramer is formed. It is preferred to purify the resulting protein by gel filtration or the like in each step above.

The HLA monomer, dimer, tetramer and pentamer described above are used effectively as a detecting agent for CTLs which are specific for livin-derived HLA-A24-binding cancer antigen peptides.

The CTL-detecting agent of the present invention can be used for the following purposes, for example.
1) To examine the frequency or amount of CTL precursors for a cancer antigen peptide of the present invention before the initiation of treatment with cancer antigen peptide of the present invention. In doing so, responsiveness of a patient to the cancer antigen peptide can be assessed.
2) To examine the frequency or amount of CTLs in a patient undergoing treatment with a cancer antigen peptide (cancer vaccine) of the present invention. In doing so, it becomes possible to conduct monitoring of therapeutic effect, evaluation of suitability of treatment, and confirmation of favorable progress of treatment, and the like.

Detection of CTLs can be carried out by, specifically, isolating a biological sample (e.g., PBMC) containing CTLs from a subject patient, bringing an HLA tetramer or the like of the present invention into contact with the biological sample, and measuring the existing frequency or amount of CTLs specific for the peptide of the present invention bound to the HLA tetramer by flow cytometry, or the like.

EXAMPLES

The present invention is further illustrated by the following examples, but is not limited by these examples in any respect.

Example 1

Investigation of Binding Affinity of a Peptide to HLA-A*2402

Eight peptides possibly binding to HLA-A*2402 (a kind of HLA-A24) were synthesized on the basis of amino acid sequence of livin (NCBI database Entrez, AAG33622). The respective peptides have amino acid sequences corresponding to the following positions on livin.
47-55: peptide 1: Ala Trp Asp His Val Asp Gly Gln Ile (SEQ ID NO: 2)
47-56: peptide 2: Ala Trp Asp His Val Asp Gly Gln Ile Leu (SEQ ID NO: 3)
80-89: peptide 3: Ala Phe Pro Gly Met Gly Ser Glu Glu Leu (SEQ ID NO: 4)
83-91: peptide 4: Gly Met Gly Ser Glu Glu Leu Arg Leu (SEQ ID NO: 5)
140-148: peptide 5: Pro Trp Thr Glu His Ala Lys Trp Phe (SEQ ID NO: 6)
146-154: peptide 6: Lys Trp Phe Pro Ser Cys Gln Phe Leu (SEQ ID NO: 7)
146-155: peptide 7: Lys Trp Phe Pro Ser Cys Gln Phe Leu Leu (SEQ ID NO: 8)
145-154: peptide 8: Ala Lys Trp Phe Pro Ser Cys Gln Phe Leu (SEQ ID NO: 9)

These peptides derived from livin and a peptide (Thr Tyr Gly Pro Val Phe Met Ser Leu; SEQ ID NO: 60) derived from EB virus were synthesized by F-moc method using an amino acid synthesizer.

The binding affinity of these peptides to HLA-A*2402 was determined according a similar method to that described in *J. Immunol.* 164:2565, 2000. A cell line, RMA-S-A*2402 cell (*J. Immunol.*, 164, 2565-2574 (2000)) obtained by introducing a chimera MHC gene composed of HLA-A*2402 and H-2K$^b$ into mouse lymphoma cell line RMA-S which does not express MHC class I molecule was incubated at 26° C. for 18 hours. RMA-S-A*2402 cells were washed with a PBS solution, suspended in a culture solution OPTI-MEM (Invitrogen) containing 3 μL/mL human β2-microglobulin and 100 μL/mL of each peptide, and incubated at 26° C. for 3 hours, and at 37° C. for 3 hours. The cells were washed with a PBS solution and treated with anti-HLA-A24 antibody at 4° C. for 30 minutes. Furthermore, the cells were washed with a PBS solution, and treated with PE-labeled anti-mouse IgG antibody at 4° C. for 30 minutes. The cells were washed, and suspended in a 1 ml PBS solution containing 1% formalin for fixation. The cells were measured by a device for flow cytometry (FACScan, BD Bioscience), and the binding affinity of a peptide was obtained from the mean fluorescence intensity. The binding affinity of the eight peptides above is shown in FIG. 1.

The EB virus-derived peptide that has been reported to bind to HLA-A*2402 (*J. Immunol.* 158:3325, 1997) showed a strong binding affinity. The results showed that peptides 5, 6, 7 and 8 among eight peptides tested bind to HLA-A*2402 favorably. In particular, peptide 7 showed higher binding affinity than the positive control (EBV).

Example 2

Induction of CTLs from Human Peripheral Blood Mononuclear Cells by Livin-derived Peptides CTLs were induced from peripheral blood mononuclear cells using the peptide 7 (SEQ ID NO: 8) that showed potent binding affinity to HLA-A*2402 in Example 1 according to the same method that described in a literature (*J. Immunol.* 169:1611, 2002). After obtaining informed-consent, peripheral blood was collected from an HLA-A24-positive patient having lung cancer, and mononuclear cells were separated by density gradient centrifugation method and cultured in AIM-V culture solution (Invitrogen). After 24-hour-cultivation, nonadherent cells were recovered and cultured in AIM-V containing 100 U/mL IL-2. For the preparation of antigen-presenting cells, adherent cells were cultured in AIM-V culture solution containing 1000 U/mL IL-4 and 1000 U/mL GM-CSF for 5 days, and, after addition of 10 μM peptide 7, cultured for another 1 day. To the culture were then added 10 ng/mL TNF and 1000 U/mL IFN-α, and the mixture was cultured. CD8-positive T cells were separated from the nonadherent cells by means of anti-CD8 antibody-bound magnetic beads, and cultured together with antigen-presenting cells pulsed with a peptide as described above.

Figure 2:
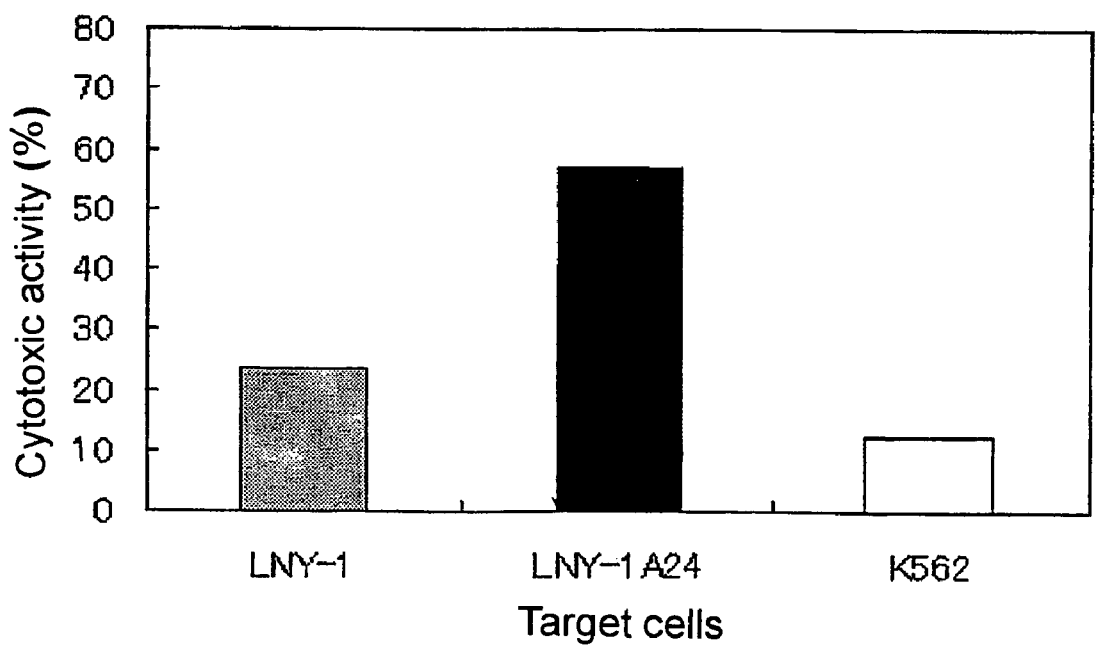
FIG. 2 is a graph showing the results of $^{51}$Cr release assay wherein a livin-derived peptide (peptide 7) was examined for the activity of inducing CTLs from human peripheral blood mononuclear cells (PBMCs). PBMCs isolated from an HLA- A24-positive lung cancer patient were used. In the figure, the vertical axis shows the cytotoxic activity of CTLs. Of the target cells shown in the figure, LNY-1 is livin-positive and HLA-A*2402-negative; LNY-1A24 is livin-positive and HLA-A*2402-positive, K562 is livin-negative and HLA-A*2402-negative (Example 2).
Figure 3:
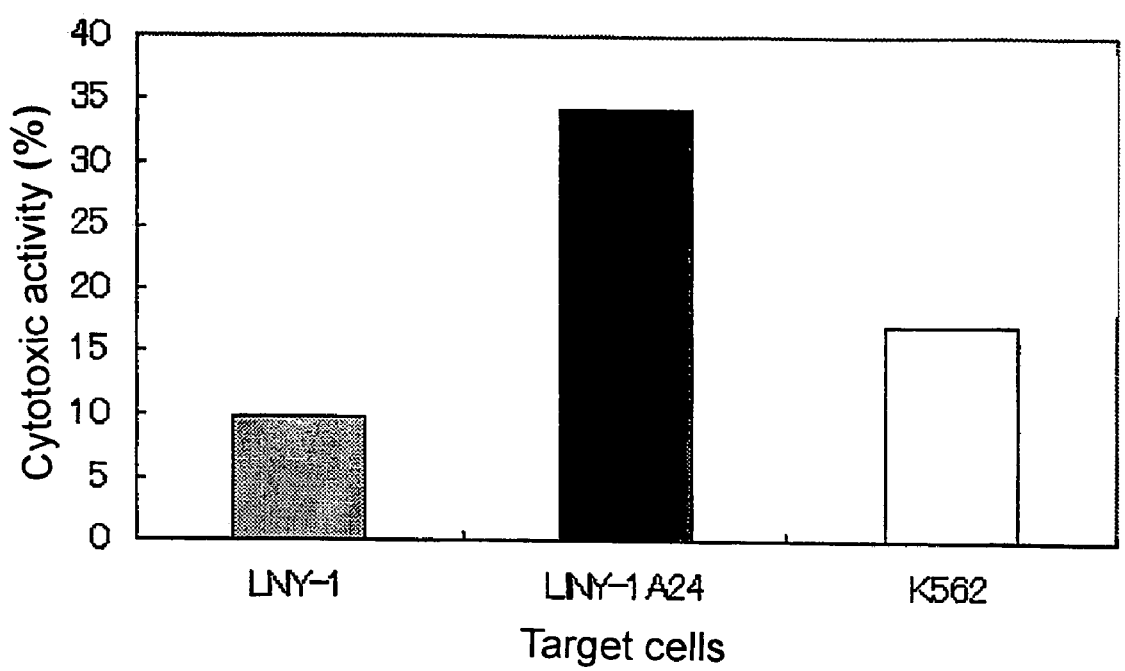
FIG. 3 is a graph showing the results obtained in the same experiment as that shown in FIG. 2 except that PBMCs were obtained from a different HLA-A24-positive lung cancer patient.

The remaining nonadhesive cells after separating CD8-positive T cells were cultured in AIM-V medium containing 1 μg/mL PHA and 100 U/mL IL-2 for 3 days, then in a medium lacking PHA for 4 days, and stocked as antigen presenting cells for the second and third peptide-stimulation. The CD8-positive T cells that had received peptide-stimulation were subjected to the second and third peptide-stimulation on 7 and 14 days after the first peptide-stimulation by adding the stocked antigen presenting cells having been pulsed with peptide 7 for 2 hours and X-ray radiated (5000 rad). After one week from the third stimulation, cytotoxic activity of T cells was measured by $^{51}$Cr release assay. The following cells were used as the target cells: livin-positive and HLA-A*2402-negative LNY-1 cell (a cell line derived from lung cancer); LNY-1A24 cell obtained from LNY-1 cell by introducing HLA-A*2402 gene stably; and livin-negative and HLA-A*2402-negative K562 (ATCC strain No. CCL-243) which is a cell line derived from chronic myelogenous leukemia and is sensitive to NK cell. The target cells were labeled with 100 μCi $^{51}$Cr for one hour. To $5\times10^3$ target cells were added 10-fold of effector cells (T cells stimulated with a peptide). After culturing for 4 hours, the cytotoxic activity was measured. The results obtained in two subject patients are shown in FIGS. 2 and 3.

T cells stimulated with peptide 7 injured livin-positive and HLA-A*2402-positive LNY-1A24 cells, but not livin-positive and HLA-A*2402-negative LNY-1 cells or livin-negative and HLA-A*2402-negative K562. The fact that CTLs induced by livin-derived peptide 7 injured specifically livin-expressing cells in HLA-A*2402-restricted manner indicates that the peptide 7 is an HLA-A24-binding cancer antigen peptide.

INDUSTRIAL APPLICABILITY

According to the present invention, it is provided an HLA-A24 binding cancer antigen peptide, a polynucleotide encoding said peptide, a CTL inducer comprising the peptide or polynucleotide, and the like. The CTL inducer of the present invention is useful as cancer vaccine. The cancer vaccine of the present invention is applicable to many HLA-A24-positive patients having cancer.

SEQUENCE LISTING FREE TEXT

The amino acid sequence set forth in SEQ ID NO: 2 is a synthetic peptide.
The amino acid sequence set forth in SEQ ID NO: 3 is a synthetic peptide.
The amino acid sequence set forth in SEQ ID NO: 4 is a synthetic peptide.
The amino acid sequence set forth in SEQ ID NO: 5 is a synthetic peptide.
The amino acid sequence set forth in SEQ ID NO: 6 is a synthetic peptide.
The amino acid sequence set forth in SEQ ID NO: 7 is a synthetic peptide.
The amino acid sequence set forth in SEQ ID NO: 8 is a synthetic peptide.
The amino acid sequence set forth in SEQ ID NO: 9 is a synthetic peptide.
The amino acid sequence set forth in SEQ ID NO: 10 is a synthetic peptide.
The amino acid sequence set forth in SEQ ID NO: 11 is a synthetic peptide.
The amino acid sequence set forth in SEQ ID NO: 12 is a synthetic peptide.
The amino acid sequence set forth in SEQ ID NO: 13 is a synthetic peptide.
The amino acid sequence set forth in SEQ ID NO: 14 is a synthetic peptide.
The amino acid sequence set forth in SEQ ID NO: 15 is a synthetic peptide.
The amino acid sequence set forth in SEQ ID NO: 16 is a synthetic peptide.
The amino acid sequence set forth in SEQ ID NO: 17 is a synthetic peptide.
The amino acid sequence set forth in SEQ ID NO: 18 is a synthetic peptide.
The amino acid sequence set forth in SEQ ID NO: 19 is a synthetic peptide.
The amino acid sequence set forth in SEQ ID NO: 20 is a synthetic peptide.
The amino acid sequence set forth in SEQ ID NO: 21 is a synthetic peptide.
The amino acid sequence set forth in SEQ ID NO: 22 is a synthetic peptide.
The amino acid sequence set forth in SEQ ID NO: 23 is a synthetic peptide.
The amino acid sequence set forth in SEQ ID NO: 24 is a synthetic peptide.
The amino acid sequence set forth in SEQ ID NO: 25 is a synthetic peptide.
The amino acid sequence set forth in SEQ ID NO: 26 is a synthetic peptide.
The amino acid sequence set forth in SEQ ID NO: 27 is a synthetic peptide.
The amino acid sequence set forth in SEQ ID NO: 28 is a synthetic peptide.
The amino acid sequence set forth in SEQ ID NO: 29 is a synthetic peptide.
The amino acid sequence set forth in SEQ ID NO: 30 is a synthetic peptide.
The amino acid sequence set forth in SEQ ID NO: 31 is a synthetic peptide.
The amino acid sequence set forth in SEQ ID NO: 32 is a synthetic peptide.
The amino acid sequence set forth in SEQ ID NO: 33 is a synthetic peptide.
The amino acid sequence set forth in SEQ ID NO: 34 is a synthetic peptide.
The amino acid sequence set forth in SEQ ID NO: 35 is a synthetic peptide.
The amino acid sequence set forth in SEQ ID NO: 36 is a synthetic peptide.
The amino acid sequence set forth in SEQ ID NO: 37 is a synthetic peptide.
The amino acid sequence set forth in SEQ ID NO: 38 is a synthetic peptide.
The amino acid sequence set forth in SEQ ID NO: 39 is a synthetic peptide.
The amino acid sequence set forth in SEQ ID NO: 40 is a synthetic peptide.
The amino acid sequence set forth in SEQ ID NO: 41 is a synthetic peptide.
The amino acid sequence set forth in SEQ ID NO: 42 is a synthetic peptide.
The amino acid sequence set forth in SEQ ID NO: 43 is a synthetic peptide.
The amino acid sequence set forth in SEQ ID NO: 44 is a synthetic peptide.

The amino acid sequence set forth in SEQ ID NO: 45 is a synthetic peptide.
The amino acid sequence set forth in SEQ ID NO: 46 is a synthetic peptide.
The amino acid sequence set forth in SEQ ID NO: 47 is a synthetic peptide.
The amino acid sequence set forth in SEQ ID NO: 48 is a synthetic peptide.
The amino acid sequence set forth in SEQ ID NO: 49 is a synthetic peptide.
The amino acid sequence set forth in SEQ ID NO: 50 is a synthetic peptide.
The amino acid sequence set forth in SEQ ID NO: 51 is a synthetic peptide.
The amino acid sequence set forth in SEQ ID NO: 52 is a synthetic peptide.
The amino acid sequence set forth in SEQ ID NO: 53 is a synthetic peptide.
The amino acid sequence set forth in SEQ ID NO: 54 is a synthetic peptide.
The amino acid sequence set forth in SEQ ID NO: 55 is a synthetic peptide.
The amino acid sequence set forth in SEQ ID NO: 56 is a synthetic peptide.
The amino acid sequence set forth in SEQ ID NO: 57 is a synthetic peptide.
The amino acid sequence set forth in SEQ ID NO: 58 is a synthetic peptide.
The amino acid sequence set forth in SEQ ID NO: 59 is a synthetic peptide.
The amino acid sequence set forth in SEQ ID NO: 60 is a synthetic peptide.
The amino acid sequence set forth in SEQ ID NO: 61 is a synthetic peptide.
The amino acid sequence set forth in SEQ ID NO: 62 is a synthetic peptide.
In the amino acid sequence set forth in SEQ ID NO: 63, the amino acid residue Xaa at position 2 is phenylalanine residue (Phe), tyrosine residue (Tyr), methionine residue (Met) or tryptophan residue (Trp), and the amino cid residue Xaa at position 10 is phenylalanine residue (Phe), leucine residue (Leu), isoleucine residue (Ile), tryptophan residue (Trp) or methionine residue (Met).

---

The invention claimed is:

1. A peptide of 10-11 amino acids which comprises an amino acid sequence set forth in SEQ ID NO: 8, which binds to an HLA-A24 antigen and is recognized by cytotoxic T lymphocytes.

2. A peptide of 10-11 amino acids which comprises an amino acid sequence wherein the amino acid residue at position 2 and/or C-terminus of an amino acid sequence set forth in SEQ ID NO: 8 is substituted by an amino acid residue selected from the group consisting of the following amino acids for the position 2: tyrosine, phenylalanine, methionine and tryptophan; and selected from the group consisting of the following amino acids for the C-terminus: phenylalanine, leucine, isoleucine, tryptophan and methionine; wherein said peptide binds to an HLA-A24 antigen and is recognized by cytotoxic T lymphocytes.

3. The peptide of claim 1, that consists of an amino acid sequence set forth in SEQ ID NO: 8.

4. The peptide according to claim 2, which consists of an amino acid sequence wherein the amino acid residue at position 2 and/or C-terminus of an amino acid sequence set forth in SEQ ID NO: 8 is substituted by an amino acid residue selected from the group consisting of the following amino acids for the position 2: tyrosine, phenylalanine, methionine and tryptophan; and selected from the group consisting of the following amino acids for the C-terminus: phenylalanine, leucine, isoleucine, tryptophan and methionine.

5. An epitope peptide comprising a peptide according to any one of claims 1-4.

* * * * *

UNITED STATES PATENT AND TRADEMARK OFFICE
CERTIFICATE OF CORRECTION

| | |
|---|---|
| PATENT NO. | : 7,601,801 B2 |
| APPLICATION NO. | : 10/563916 |
| DATED | : October 13, 2009 |
| INVENTOR(S) | : Sato et al. |

Page 1 of 1

It is certified that error appears in the above-identified patent and that said Letters Patent is hereby corrected as shown below:

On the Title Pg,

Item [*] Notice:   Subject to any disclaimer, the term of this patent is extended or adjusted under 35 USC 154(b) by 186 days Delete the phrase "by 186 days" and insert -- by 373 days --

Signed and Sealed this

Twenty-fifth Day of May, 2010

David J. Kappos
*Director of the United States Patent and Trademark Office*

SEQUENCE LISTING

```
<160> NUMBER OF SEQ ID NOS: 63

<210> SEQ ID NO 1
<211> LENGTH: 280
<212> TYPE: PRT
<213> ORGANISM: Homo sapiens

<400> SEQUENCE: 1

Met Gly Pro Lys Asp Ser Ala Lys Cys Leu His Arg Gly Pro Gln Pro
 1               5                  10                  15

Ser His Trp Ala Ala Gly Asp Gly Pro Thr Gln Glu Arg Cys Gly Pro
                20                  25                  30

Arg Ser Leu Gly Ser Pro Val Leu Gly Leu Asp Thr Cys Arg Ala Trp
            35                  40                  45

Asp His Val Asp Gly Gln Ile Leu Gly Gln Leu Arg Pro Leu Thr Glu
        50                  55                  60

Glu Glu Glu Glu Gly Ala Gly Ala Thr Leu Ser Arg Gly Pro Ala
65                  70                  75                  80

Phe Pro Gly Met Gly Ser Glu Glu Leu Arg Leu Ala Ser Phe Tyr Asp
                85                  90                  95

Trp Pro Leu Thr Ala Glu Val Pro Pro Glu Leu Leu Ala Ala Ala Gly
            100                 105                 110

Phe Phe His Thr Gly His Gln Asp Lys Val Arg Cys Phe Phe Cys Tyr
        115                 120                 125

Gly Gly Leu Gln Ser Trp Lys Arg Gly Asp Asp Pro Trp Thr Glu His
    130                 135                 140

Ala Lys Trp Phe Pro Ser Cys Gln Phe Leu Leu Arg Ser Lys Gly Arg
145                 150                 155                 160

Asp Phe Val His Ser Val Gln Glu Thr His Ser Gln Leu Leu Gly Ser
                165                 170                 175

Trp Asp Pro Trp Glu Glu Pro Glu Asp Ala Ala Pro Val Ala Pro Ser
            180                 185                 190

Val Pro Ala Ser Gly Tyr Pro Glu Leu Pro Thr Pro Arg Arg Glu Val
        195                 200                 205
```

```
Gln Ser Glu Ser Ala Gln Glu Pro Gly Ala Arg Asp Val Glu Ala Gln
    210                 215                 220
Leu Arg Arg Leu Gln Glu Glu Arg Thr Cys Lys Val Cys Leu Asp Arg
225                 230                 235                 240
Ala Val Ser Ile Val Phe Val Pro Cys Gly His Leu Val Cys Ala Glu
                245                 250                 255
Cys Ala Pro Gly Leu Gln Leu Cys Pro Ile Cys Arg Ala Pro Val Arg
            260                 265                 270
Ser Arg Val Arg Thr Phe Leu Ser
        275                 280

<210> SEQ ID NO 2
<211> LENGTH: 9
<212> TYPE: PRT
<213> ORGANISM: Artificial Sequence
<220> FEATURE:
<223> OTHER INFORMATION: HLA-A24 binding cancer antigen peptide derived
      from livin

<400> SEQUENCE: 2

Ala Trp Asp His Val Asp Gly Gln Ile
1               5

<210> SEQ ID NO 3
<211> LENGTH: 10
<212> TYPE: PRT
<213> ORGANISM: Artificial Sequence
<220> FEATURE:
<223> OTHER INFORMATION: HLA-A24 binding cancer antigen peptide derived
      from livin

<400> SEQUENCE: 3

Ala Trp Asp His Val Asp Gly Gln Ile Leu
1               5                   10

<210> SEQ ID NO 4
<211> LENGTH: 10
<212> TYPE: PRT
<213> ORGANISM: Artificial Sequence
<220> FEATURE:
<223> OTHER INFORMATION: HLA-A24 binding cancer antigen peptide derived
      from livin

<400> SEQUENCE: 4

Ala Phe Pro Gly Met Gly Ser Glu Glu Leu
1               5                   10

<210> SEQ ID NO 5
<211> LENGTH: 9
<212> TYPE: PRT
<213> ORGANISM: Artificial Sequence
<220> FEATURE:
<223> OTHER INFORMATION: HLA-A24 binding cancer antigen peptide derived
      from livin

<400> SEQUENCE: 5

Gly Met Gly Ser Glu Glu Leu Arg Leu
1               5

<210> SEQ ID NO 6
<211> LENGTH: 9
<212> TYPE: PRT
<213> ORGANISM: Artificial Sequence
<220> FEATURE:
<223> OTHER INFORMATION: HLA-A24 binding cancer antigen peptide derived
```

```
        from livin

<400> SEQUENCE: 6

Pro Trp Thr Glu His Ala Lys Trp Phe
1               5

<210> SEQ ID NO 7
<211> LENGTH: 9
<212> TYPE: PRT
<213> ORGANISM: Artificial Sequence
<220> FEATURE:
<223> OTHER INFORMATION: HLA-A24 binding cancer antigen peptide derived
        from livin

<400> SEQUENCE: 7

Lys Trp Phe Pro Ser Cys Gln Phe Leu
1               5

<210> SEQ ID NO 8
<211> LENGTH: 10
<212> TYPE: PRT
<213> ORGANISM: Artificial Sequence
<220> FEATURE:
<223> OTHER INFORMATION: HLA-A24 binding cancer antigen peptide derived
        from livin

<400> SEQUENCE: 8

Lys Trp Phe Pro Ser Cys Gln Phe Leu Leu
1               5                   10

<210> SEQ ID NO 9
<211> LENGTH: 10
<212> TYPE: PRT
<213> ORGANISM: Artificial Sequence
<220> FEATURE:
<223> OTHER INFORMATION: HLA-A24 binding cancer antigen peptide derived
        from livin

<400> SEQUENCE: 9

Ala Lys Trp Phe Pro Ser Cys Gln Phe Leu
1               5                   10

<210> SEQ ID NO 10
<211> LENGTH: 9
<212> TYPE: PRT
<213> ORGANISM: Artificial Sequence
<220> FEATURE:
<223> OTHER INFORMATION: HLA-A24 binding cancer antigen peptide derived
        from livin

<400> SEQUENCE: 10

Trp Phe Pro Ser Cys Gln Phe Leu Leu
1               5

<210> SEQ ID NO 11
<211> LENGTH: 9
<212> TYPE: PRT
<213> ORGANISM: Artificial Sequence
<220> FEATURE:
<223> OTHER INFORMATION: HLA-A24 binding cancer antigen peptide derived
        from livin

<400> SEQUENCE: 11

Arg Cys Phe Phe Cys Tyr Gly Gly Leu
1               5

<210> SEQ ID NO 12
```

```
<211> LENGTH: 9
<212> TYPE: PRT
<213> ORGANISM: Artificial Sequence
<220> FEATURE:
<223> OTHER INFORMATION: HLA-A24 binding cancer antigen peptide derived
      from livin

<400> SEQUENCE: 12

Leu Thr Ala Glu Val Pro Pro Glu Leu
1               5

<210> SEQ ID NO 13
<211> LENGTH: 9
<212> TYPE: PRT
<213> ORGANISM: Artificial Sequence
<220> FEATURE:
<223> OTHER INFORMATION: HLA-A24 binding cancer antigen peptide derived
      from livin

<400> SEQUENCE: 13

Val Gln Glu Thr His Ser Gln Leu Leu
1               5

<210> SEQ ID NO 14
<211> LENGTH: 9
<212> TYPE: PRT
<213> ORGANISM: Artificial Sequence
<220> FEATURE:
<223> OTHER INFORMATION: HLA-A24 binding cancer antigen peptide derived
      from livin

<400> SEQUENCE: 14

Ser Val Gln Glu Thr His Ser Gln Leu
1               5

<210> SEQ ID NO 15
<211> LENGTH: 9
<212> TYPE: PRT
<213> ORGANISM: Artificial Sequence
<220> FEATURE:
<223> OTHER INFORMATION: HLA-A24 binding cancer antigen peptide derived
      from livin

<400> SEQUENCE: 15

Gly Ala Arg Asp Val Glu Ala Gln Leu
1               5

<210> SEQ ID NO 16
<211> LENGTH: 9
<212> TYPE: PRT
<213> ORGANISM: Artificial Sequence
<220> FEATURE:
<223> OTHER INFORMATION: HLA-A24 binding cancer antigen peptide derived
      from livin

<400> SEQUENCE: 16

Thr Ala Glu Val Pro Pro Glu Leu Leu
1               5

<210> SEQ ID NO 17
<211> LENGTH: 9
<212> TYPE: PRT
<213> ORGANISM: Artificial Sequence
<220> FEATURE:
<223> OTHER INFORMATION: HLA-A24 binding cancer antigen peptide derived
      from livin

<400> SEQUENCE: 17
```

-continued

Gln Ile Gly Gln Leu Arg Pro Leu
1               5

<210> SEQ ID NO 18
<211> LENGTH: 9
<212> TYPE: PRT
<213> ORGANISM: Artificial Sequence
<220> FEATURE:
<223> OTHER INFORMATION: HLA-A24 binding cancer antigen peptide derived
      from livin

<400> SEQUENCE: 18

Asp Val Glu Ala Gln Leu Arg Arg Leu
1               5

<210> SEQ ID NO 19
<211> LENGTH: 9
<212> TYPE: PRT
<213> ORGANISM: Artificial Sequence
<220> FEATURE:
<223> OTHER INFORMATION: HLA-A24 binding cancer antigen peptide derived
      from livin

<400> SEQUENCE: 19

Gly Pro Lys Asp Ser Ala Lys Cys Leu
1               5

<210> SEQ ID NO 20
<211> LENGTH: 9
<212> TYPE: PRT
<213> ORGANISM: Artificial Sequence
<220> FEATURE:
<223> OTHER INFORMATION: HLA-A24 binding cancer antigen peptide derived
      from livin

<400> SEQUENCE: 20

Val Cys Ala Glu Cys Ala Pro Gly Leu
1               5

<210> SEQ ID NO 21
<211> LENGTH: 9
<212> TYPE: PRT
<213> ORGANISM: Artificial Sequence
<220> FEATURE:
<223> OTHER INFORMATION: HLA-A24 binding cancer antigen peptide derived
      from livin

<400> SEQUENCE: 21

Val Pro Ala Ser Gly Tyr Pro Glu Leu
1               5

<210> SEQ ID NO 22
<211> LENGTH: 9
<212> TYPE: PRT
<213> ORGANISM: Artificial Sequence
<220> FEATURE:
<223> OTHER INFORMATION: HLA-A24 binding cancer antigen peptide derived
      from livin

<400> SEQUENCE: 22

Phe Pro Gly Met Gly Ser Glu Glu Leu
1               5

<210> SEQ ID NO 23
<211> LENGTH: 9
<212> TYPE: PRT
<213> ORGANISM: Artificial Sequence
<220> FEATURE:

```
<223> OTHER INFORMATION: HLA-A24 binding cancer antigen peptide derived
      from livin

<400> SEQUENCE: 23

Leu Ala Ser Phe Tyr Asp Trp Pro Leu
1               5

<210> SEQ ID NO 24
<211> LENGTH: 9
<212> TYPE: PRT
<213> ORGANISM: Artificial Sequence
<220> FEATURE:
<223> OTHER INFORMATION: HLA-A24 binding cancer antigen peptide derived
      from livin

<400> SEQUENCE: 24

Ile Val Phe Val Pro Cys Gly His Leu
1               5

<210> SEQ ID NO 25
<211> LENGTH: 9
<212> TYPE: PRT
<213> ORGANISM: Artificial Sequence
<220> FEATURE:
<223> OTHER INFORMATION: HLA-A24 binding cancer antigen peptide derived
      from livin

<400> SEQUENCE: 25

Ser Leu Gly Ser Pro Val Leu Gly Leu
1               5

<210> SEQ ID NO 26
<211> LENGTH: 9
<212> TYPE: PRT
<213> ORGANISM: Artificial Sequence
<220> FEATURE:
<223> OTHER INFORMATION: HLA-A24 binding cancer antigen peptide derived
      from livin

<400> SEQUENCE: 26

Glu Leu Leu Ala Ala Ala Gly Phe Phe
1               5

<210> SEQ ID NO 27
<211> LENGTH: 9
<212> TYPE: PRT
<213> ORGANISM: Artificial Sequence
<220> FEATURE:
<223> OTHER INFORMATION: HLA-A24 binding cancer antigen peptide derived
      from livin

<400> SEQUENCE: 27

Ala Thr Leu Ser Arg Gly Pro Ala Phe
1               5

<210> SEQ ID NO 28
<211> LENGTH: 9
<212> TYPE: PRT
<213> ORGANISM: Artificial Sequence
<220> FEATURE:
<223> OTHER INFORMATION: HLA-A24 binding cancer antigen peptide derived
      from livin

<400> SEQUENCE: 28

His Gln Asp Lys Val Arg Cys Phe Phe
1               5
```

<210> SEQ ID NO 29
<211> LENGTH: 9
<212> TYPE: PRT
<213> ORGANISM: Artificial Sequence
<220> FEATURE:
<223> OTHER INFORMATION: HLA-A24 binding cancer antigen peptide derived
      from livin

<400> SEQUENCE: 29

Leu Leu Arg Ser Lys Gly Arg Asp Phe
1               5

<210> SEQ ID NO 30
<211> LENGTH: 9
<212> TYPE: PRT
<213> ORGANISM: Artificial Sequence
<220> FEATURE:
<223> OTHER INFORMATION: HLA-A24 binding cancer antigen peptide derived
      from livin

<400> SEQUENCE: 30

Val Cys Leu Asp Arg Ala Val Ser Ile
1               5

<210> SEQ ID NO 31
<211> LENGTH: 9
<212> TYPE: PRT
<213> ORGANISM: Artificial Sequence
<220> FEATURE:
<223> OTHER INFORMATION: HLA-A24 binding cancer antigen peptide derived
      from livin

<400> SEQUENCE: 31

Gly Tyr Pro Glu Leu Pro Thr Pro Arg
1               5

<210> SEQ ID NO 32
<211> LENGTH: 9
<212> TYPE: PRT
<213> ORGANISM: Artificial Sequence
<220> FEATURE:
<223> OTHER INFORMATION: HLA-A24 binding cancer antigen peptide derived
      from livin

<400> SEQUENCE: 32

Ala Pro Gly Leu Gln Leu Cys Pro Ile
1               5

<210> SEQ ID NO 33
<211> LENGTH: 10
<212> TYPE: PRT
<213> ORGANISM: Artificial Sequence
<220> FEATURE:
<223> OTHER INFORMATION: HLA-A24 binding cancer antigen peptide derived
      from livin

<400> SEQUENCE: 33

Arg Ser Leu Gly Ser Pro Val Leu Gly Leu
1               5                   10

<210> SEQ ID NO 34
<211> LENGTH: 10
<212> TYPE: PRT
<213> ORGANISM: Artificial Sequence
<220> FEATURE:
<223> OTHER INFORMATION: HLA-A24 binding cancer antigen peptide derived
      from livin

<400> SEQUENCE: 34

Ser Val Gln Glu Thr His Ser Gln Leu Leu
1               5                   10

<210> SEQ ID NO 35
<211> LENGTH: 10
<212> TYPE: PRT
<213> ORGANISM: Artificial Sequence
<220> FEATURE:
<223> OTHER INFORMATION: HLA-A24 binding cancer antigen peptide derived
      from livin

<400> SEQUENCE: 35

Arg Leu Ala Ser Phe Tyr Asp Trp Pro Leu
1               5                   10

<210> SEQ ID NO 36
<211> LENGTH: 10
<212> TYPE: PRT
<213> ORGANISM: Artificial Sequence
<220> FEATURE:
<223> OTHER INFORMATION: HLA-A24 binding cancer antigen peptide derived
      from livin

<400> SEQUENCE: 36

Phe Tyr Asp Trp Pro Leu Thr Ala Glu Val
1               5                   10

<210> SEQ ID NO 37
<211> LENGTH: 10
<212> TYPE: PRT
<213> ORGANISM: Artificial Sequence
<220> FEATURE:
<223> OTHER INFORMATION: HLA-A24 binding cancer antigen peptide derived
      from livin

<400> SEQUENCE: 37

Ser Val Pro Ala Ser Gly Tyr Pro Glu Leu
1               5                   10

<210> SEQ ID NO 38
<211> LENGTH: 10
<212> TYPE: PRT
<213> ORGANISM: Artificial Sequence
<220> FEATURE:
<223> OTHER INFORMATION: HLA-A24 binding cancer antigen peptide derived
      from livin

<400> SEQUENCE: 38

Met Gly Pro Lys Asp Ser Ala Lys Cys Leu
1               5                   10

<210> SEQ ID NO 39
<211> LENGTH: 10
<212> TYPE: PRT
<213> ORGANISM: Artificial Sequence
<220> FEATURE:
<223> OTHER INFORMATION: HLA-A24 binding cancer antigen peptide derived
      from livin

<400> SEQUENCE: 39

Ser Ile Val Phe Val Pro Cys Gly His Leu
1               5                   10

<210> SEQ ID NO 40
<211> LENGTH: 10
<212> TYPE: PRT
<213> ORGANISM: Artificial Sequence -continued

```
<220> FEATURE:
<223> OTHER INFORMATION: HLA-A24 binding cancer antigen peptide derived
      from livin

<400> SEQUENCE: 40

Thr Gln Glu Arg Cys Gly Pro Arg Ser Leu
1               5                   10

<210> SEQ ID NO 41
<211> LENGTH: 10
<212> TYPE: PRT
<213> ORGANISM: Artificial Sequence
<220> FEATURE:
<223> OTHER INFORMATION: HLA-A24 binding cancer antigen peptide derived
      from livin

<400> SEQUENCE: 41

His Ser Val Gln Glu Thr His Ser Gln Leu
1               5                   10

<210> SEQ ID NO 42
<211> LENGTH: 10
<212> TYPE: PRT
<213> ORGANISM: Artificial Sequence
<220> FEATURE:
<223> OTHER INFORMATION: HLA-A24 binding cancer antigen peptide derived
      from livin

<400> SEQUENCE: 42

Cys Ala Glu Cys Ala Pro Gly Leu Gln Leu
1               5                   10

<210> SEQ ID NO 43
<211> LENGTH: 10
<212> TYPE: PRT
<213> ORGANISM: Artificial Sequence
<220> FEATURE:
<223> OTHER INFORMATION: HLA-A24 binding cancer antigen peptide derived
      from livin

<400> SEQUENCE: 43

Gly Gln Ile Leu Gly Gln Leu Arg Pro Leu
1               5                   10

<210> SEQ ID NO 44
<211> LENGTH: 10
<212> TYPE: PRT
<213> ORGANISM: Artificial Sequence
<220> FEATURE:
<223> OTHER INFORMATION: HLA-A24 binding cancer antigen peptide derived
      from livin

<400> SEQUENCE: 44

His Val Asp Gly Gln Ile Leu Gly Gln Leu
1               5                   10

<210> SEQ ID NO 45
<211> LENGTH: 10
<212> TYPE: PRT
<213> ORGANISM: Artificial Sequence
<220> FEATURE:
<223> OTHER INFORMATION: HLA-A24 binding cancer antigen peptide derived
      from livin

<400> SEQUENCE: 45

Leu Thr Ala Glu Val Pro Pro Glu Leu Leu
1               5                   10
```

```
<210> SEQ ID NO 46
<211> LENGTH: 10
<212> TYPE: PRT
<213> ORGANISM: Artificial Sequence
<220> FEATURE:
<223> OTHER INFORMATION: HLA-A24 binding cancer antigen peptide derived
      from livin

<400> SEQUENCE: 46

Gly Pro Arg Ser Leu Gly Ser Pro Val Leu
1               5                   10

<210> SEQ ID NO 47
<211> LENGTH: 10
<212> TYPE: PRT
<213> ORGANISM: Artificial Sequence
<220> FEATURE:
<223> OTHER INFORMATION: HLA-A24 binding cancer antigen peptide derived
      from livin

<400> SEQUENCE: 47

Leu Val Cys Ala Glu Cys Ala Pro Gly Leu
1               5                   10

<210> SEQ ID NO 48
<211> LENGTH: 10
<212> TYPE: PRT
<213> ORGANISM: Artificial Sequence
<220> FEATURE:
<223> OTHER INFORMATION: HLA-A24 binding cancer antigen peptide derived
      from livin

<400> SEQUENCE: 48

Gly Ser Glu Glu Leu Arg Leu Ala Ser Phe
1               5                   10

<210> SEQ ID NO 49
<211> LENGTH: 10
<212> TYPE: PRT
<213> ORGANISM: Artificial Sequence
<220> FEATURE:
<223> OTHER INFORMATION: HLA-A24 binding cancer antigen peptide derived
      from livin

<400> SEQUENCE: 49

Arg Ala Trp Asp His Val Asp Gly Gln Ile
1               5                   10

<210> SEQ ID NO 50
<211> LENGTH: 10
<212> TYPE: PRT
<213> ORGANISM: Artificial Sequence
<220> FEATURE:
<223> OTHER INFORMATION: HLA-A24 binding cancer antigen peptide derived
      from livin

<400> SEQUENCE: 50

Ala Pro Val Arg Ser Arg Val Arg Thr Phe
1               5                   10

<210> SEQ ID NO 51
<211> LENGTH: 10
<212> TYPE: PRT
<213> ORGANISM: Artificial Sequence
<220> FEATURE:
<223> OTHER INFORMATION: HLA-A24 binding cancer antigen peptide derived
      from livin
```

```
<400> SEQUENCE: 51

Phe Leu Leu Arg Ser Lys Gly Arg Asp Phe
1               5                   10

<210> SEQ ID NO 52
<211> LENGTH: 10
<212> TYPE: PRT
<213> ORGANISM: Artificial Sequence
<220> FEATURE:
<223> OTHER INFORMATION: HLA-A24 binding cancer antigen peptide derived
      from livin

<400> SEQUENCE: 52

Cys Leu Asp Arg Ala Val Ser Ile Val Phe
1               5                   10

<210> SEQ ID NO 53
<211> LENGTH: 10
<212> TYPE: PRT
<213> ORGANISM: Artificial Sequence
<220> FEATURE:
<223> OTHER INFORMATION: HLA-A24 binding cancer antigen peptide derived
      from livin

<400> SEQUENCE: 53

His Ala Lys Trp Phe Pro Ser Cys Gln Phe
1               5                   10

<210> SEQ ID NO 54
<211> LENGTH: 10
<212> TYPE: PRT
<213> ORGANISM: Artificial Sequence
<220> FEATURE:
<223> OTHER INFORMATION: HLA-A24 binding cancer antigen peptide derived
      from livin

<400> SEQUENCE: 54

Asp Pro Trp Thr Glu His Ala Lys Trp Phe
1               5                   10

<210> SEQ ID NO 55
<211> LENGTH: 10
<212> TYPE: PRT
<213> ORGANISM: Artificial Sequence
<220> FEATURE:
<223> OTHER INFORMATION: HLA-A24 binding cancer antigen peptide derived
      from livin

<400> SEQUENCE: 55

Gly Ala Thr Leu Ser Arg Gly Pro Ala Phe
1               5                   10

<210> SEQ ID NO 56
<211> LENGTH: 10
<212> TYPE: PRT
<213> ORGANISM: Artificial Sequence
<220> FEATURE:
<223> OTHER INFORMATION: HLA-A24 binding cancer antigen peptide derived
      from livin

<400> SEQUENCE: 56

Thr Gly His Gln Asp Lys Val Arg Cys Phe
1               5                   10

<210> SEQ ID NO 57
<211> LENGTH: 10
<212> TYPE: PRT
```

```
<213> ORGANISM: Artificial Sequence
<220> FEATURE:
<223> OTHER INFORMATION: HLA-A24 binding cancer antigen peptide derived
      from livin

<400> SEQUENCE: 57

Lys Val Cys Leu Asp Arg Ala Val Ser Ile
1               5                   10

<210> SEQ ID NO 58
<211> LENGTH: 10
<212> TYPE: PRT
<213> ORGANISM: Artificial Sequence
<220> FEATURE:
<223> OTHER INFORMATION: HLA-A24 binding cancer antigen peptide derived
      from livin

<400> SEQUENCE: 58

Cys Ala Pro Gly Leu Gln Leu Cys Pro Ile
1               5                   10

<210> SEQ ID NO 59
<211> LENGTH: 10
<212> TYPE: PRT
<213> ORGANISM: Artificial Sequence
<220> FEATURE:
<223> OTHER INFORMATION: HLA-A24 binding cancer antigen peptide derived
      from livin

<400> SEQUENCE: 59

Arg Asp Val Glu Ala Gln Leu Arg Arg Leu
1               5                   10

<210> SEQ ID NO 60
<211> LENGTH: 9
<212> TYPE: PRT
<213> ORGANISM: Artificial Sequence
<220> FEATURE:
<223> OTHER INFORMATION: Peptide derived from EB virus

<400> SEQUENCE: 60

Thr Tyr Gly Pro Val Phe Met Ser Leu
1               5

<210> SEQ ID NO 61
<211> LENGTH: 21
<212> TYPE: PRT
<213> ORGANISM: Artificial Sequence
<220> FEATURE:
<223> OTHER INFORMATION: Tetanus toxin-originated helper peptide

<400> SEQUENCE: 61

Phe Asn Asn Phe Thr Val Ser Phe Trp Leu Arg Val Pro Lys Val Ser
1               5                   10                  15

Ala Ser His Leu Glu
            20

<210> SEQ ID NO 62
<211> LENGTH: 16
<212> TYPE: PRT
<213> ORGANISM: Artificial Sequence
<220> FEATURE:
<223> OTHER INFORMATION: Helper epitope

<400> SEQUENCE: 62

Ala Gln Tyr Ile Lys Ala Asn Ser Lys Phe Ile Gly Ile Thr Glu Leu
1               5                   10                  15
```

```
<210> SEQ ID NO 63
<211> LENGTH: 10
<212> TYPE: PRT
<213> ORGANISM: Artificial Sequence
<220> FEATURE:
<223> OTHER INFORMATION: Substitute-Type Peptide Derived From SEQ ID
      NO: 8
<220> FEATURE:
<221> NAME/KEY: MISC_FEATURE
<222> LOCATION: (2)..(2)
<223> OTHER INFORMATION: Xaa is Phe, Tyr, Met or Trp
<220> FEATURE:
<221> NAME/KEY: MISC_FEATURE
<222> LOCATION: (10)..(10)
<223> OTHER INFORMATION: Xaa is Phe, Leu, Ile, Trp or Met

<400> SEQUENCE: 63

Lys Xaa Phe Pro Ser Cys Gln Phe Leu Xaa
1               5                   10
```